US008156790B2

(12) United States Patent  
Matsuo et al.

(10) Patent No.: US 8,156,790 B2  
(45) Date of Patent: Apr. 17, 2012

(54) SENSOR AND METHOD OF PRODUCING SENSOR

(75) Inventors: Kouji Matsuo, Aichi (JP); Satoshi Ishikawa, Gifu (JP)

(73) Assignee: NGK Spark Plug Co., Ltd, Aichi (JP)

( * ) Notice: Subject to any disclaimer, the term of this patent is extended or adjusted under 35 U.S.C. 154(b) by 792 days.

(21) Appl. No.: 12/266,306

(22) Filed: Nov. 6, 2008

(65) Prior Publication Data

US 2009/0126456 A1   May 21, 2009

Related U.S. Application Data

(62) Division of application No. 10/571,785, filed as application No. PCT/JP2004/013299 on Sep. 13, 2004, now Pat. No. 7,461,538.

(30) Foreign Application Priority Data

Sep. 17, 2003 (JP) .................................. 2003-324822  
Sep. 30, 2003 (JP) .................................. 2003-341252

(51) Int. Cl.  
*G01N 7/00* (2006.01)

(52) U.S. Cl. ....... 73/31.05; 73/23.31; 204/424; 204/426

(58) Field of Classification Search ................. 73/23.31, 73/31.05; 204/424, 426  
See application file for complete search history.

(56) References Cited

U.S. PATENT DOCUMENTS

| 4,636,293 | A | 1/1987 | Bayha et al. |
| 5,098,548 | A | 3/1992 | Duce |
| 5,556,526 | A | 9/1996 | Fukaya et al. |
| 5,711,863 | A | 1/1998 | Henkelmann et al. |
| 5,922,938 | A | 7/1999 | Hafele |
| 7,340,942 | B2 * | 3/2008 | Matsuo et al. ............... 73/31.05 |
| 7,430,894 | B2 * | 10/2008 | Matsuo et al. ............... 73/31.05 |
| 7,461,538 | B2 * | 12/2008 | Matsuo et al. ............... 73/23.31 |
| 7,674,143 | B2 * | 3/2010 | Matsuo et al. ............... 439/862 |
| 2002/0148280 | A1 | 10/2002 | Weyl et al. |

FOREIGN PATENT DOCUMENTS

| JP | 61-70763 U | 4/1986 |
| JP | 61-70763 U | 5/1986 |
| JP | 1-71663 U | 5/1989 |
| JP | 2-144761 U | 12/1990 |
| JP | 2-144762 U | 12/1990 |
| JP | 6-45269 U | 6/1994 |

(Continued)

*Primary Examiner* — Daniel Larkin  
(74) *Attorney, Agent, or Firm* — Sughrue Mion, PLLC

(57) ABSTRACT

The present invention provides a sensor capable of maintaining an electrical connection between the lead frame and an electrode terminal section of the detection element even when an inadequate external force is applied to a lead frame and a sensor production method capable of preventing the lead frame from buckling and being deformed into an inadequate shape. The lead frame (second lead frame) can inhibit movement of a second frame main body section axially toward a rear end side through engagement of a third locking surface of a second locking section with a second locking groove and can inhibit the second frame main body section from going apart from an inner surface of an insertion hole through engagement of a fourth locking surface of the second frame locking section, which faces an element engagement section side. Namely, even when an external force is applied to the lead frame, movement of the lead frame main body section (second lead frame main body section) can be inhibited and a variation in the relative positions of the lead frame and the detection element can be prevented.

10 Claims, 13 Drawing Sheets

FOREIGN PATENT DOCUMENTS

| | | |
|---|---|---|
| JP | 9-102349 A | 4/1997 |
| JP | 2001-188060 A | 7/2001 |
| JP | 2001-343356 A | 12/2001 |
| JP | 2002-168824 A | 6/2002 |
| JP | 2002-296223 A | 10/2002 |
| WO | 0135087 A2 | 5/2001 |

* cited by examiner

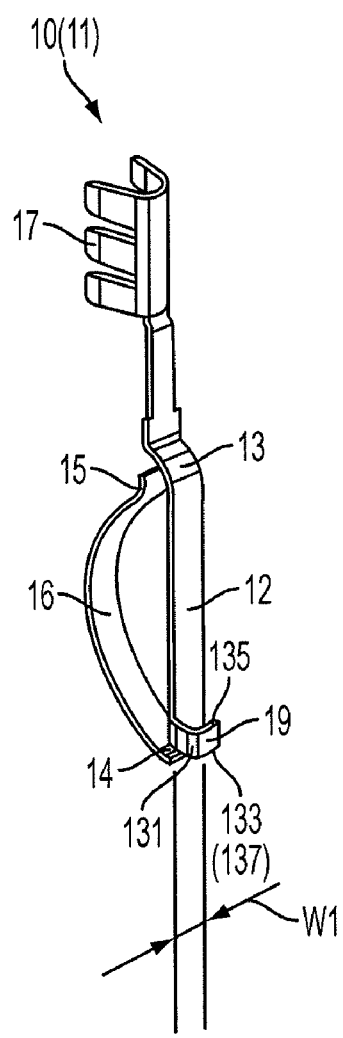
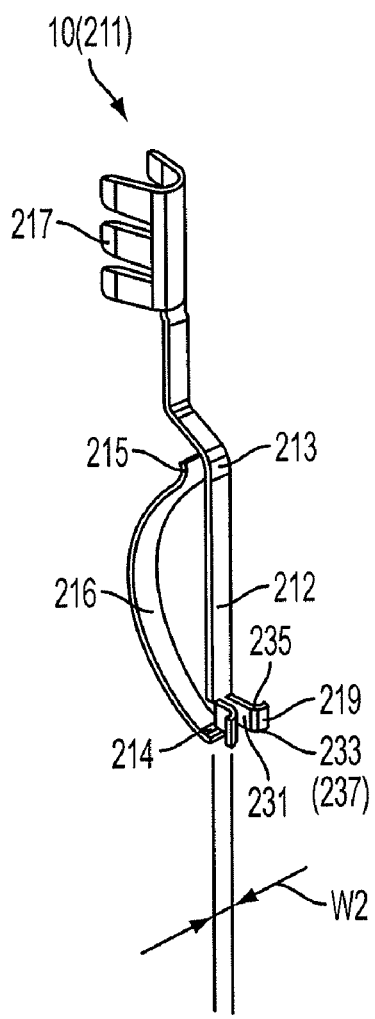

FIG. 11A
FIG. 11B
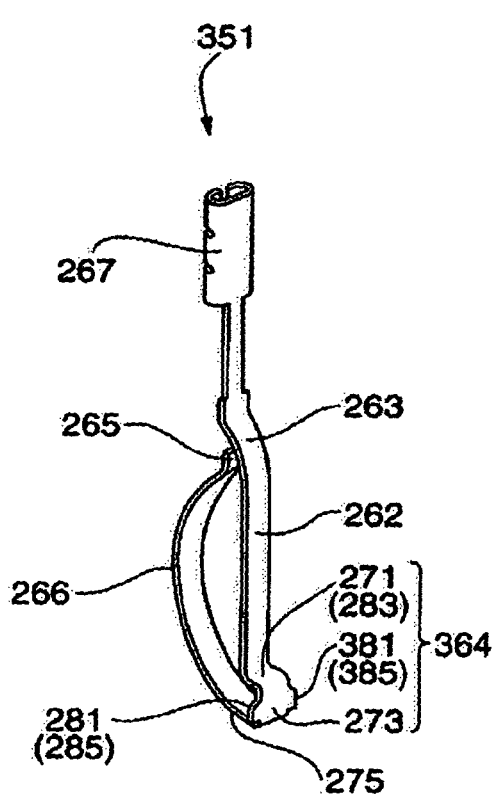
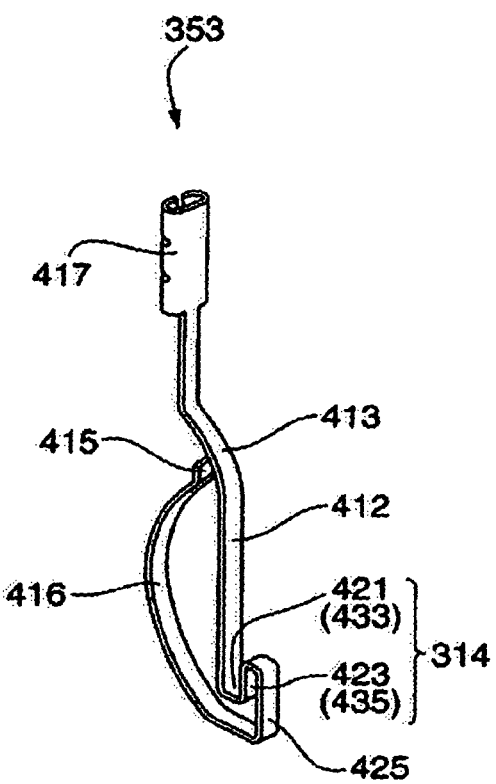

SENSOR AND METHOD OF PRODUCING SENSOR

CROSS-REFERENCE TO RELATED APPLICATION

This application is a Divisional of U.S. patent application Ser. No. 10/571,785 filed Mar. 14, 2006, now U.S. Pat. No. 7,461,538, which is a 371 of PCT Application No. PCT/JP2004/013299 filed Sep. 13, 2004 and which claims benefit of JPA No. 2003-341252 filed Sep. 30, 2003 and JPA No. 2003-324822 filed Sep. 17, 2003. The above-noted applications are incorporated herein by reference in their entirety.

TECHNICAL FIELD

This invention relates to a sensor having a detection element in the form of an axially extending plate and formed with an electrode terminal section, a separator formed with an element insertion hole for insertion of the detection element, and a metallic terminal member disposed between the detection element and an inner surface of the element insertion hole of the separator and electrically connected to the electrode terminal section to form a current path, and a method of producing such a sensor.

BACKGROUND TECHNIQUE

Heretofore, it is known a sensor having attached thereto a detection element (sensor element) in the form of an axially extending plate and formed with a detection section at a front end side to face an object to be measured. Enumerated as such a sensor are a gas sensor such as a λ (lambda) sensor, a wide-range air/fuel ratio sensor, oxygen sensor and NOx sensor, and a temperature sensor for detection of temperature.

The plate-shaped detection element is generally configured so as to have a detection section at an axial (longitudinal) front end side and an electrode terminal section at a rear end side. There is a sensor that is regarded as one having such a detection element and that is configured to electrically connect a lead frame (metallic terminal member) made of an electrically conductive material to an electrode terminal section for thereby forming a portion of an electric current path for conduction of electrical current between the detection element and an external device. In the meantime, electrical currents such as detection current (detection signal) according to a result of detection by the detection element and electrical current for power supply to a heater in case the detection element has the heater are enumerated for conduction through the electrical current path electrically connecting the detection element and the external device.

As a sensor having a lead frame is known a sensor configured to use a lead frame having a resilient contact portion that serves as a resiliently deformable (deformable by a compressive force) leaf spring and hold a detection element within an insertion hole of a separator and in a state where an electrode terminal section of the detection element is brought into contact with the resilient contact portion of the lead frame (refer to Patent Document 1).

In case of a sensor with such a structure, it becomes possible to make good the contact condition of the lead frame and the electrode terminal section of the detection element by using a lead frame configured so that a resilient contact portion exerts a large resilient force. In the meantime, as a lead frame with a resilient contact portion exerting a large resilient force are enumerated, for example, a lead frame formed so as to be large in the width size, a lead frame formed so as to be large in the thickness, etc.

Patent Document 1: Unexamined Japanese Patent Publication No. 2001-188060 (FIG. 1, FIG. 6).

However, in case the resilient contact portion of the lead frame exerts an excessively large resilient force, a large pressure more than needed is applied from the lead frame to the detection element at the time of assembly of the lead frame and the detection element, so that a damage of the detection element such as chipping or breakage may possibly be caused by that pressure.

Further, in the event a lead frame (metallic terminal member) having a large width size is used as in the above-described prior art sensor, it is necessitated a wide space for disposition of the lead frame, so that there arises a problem that such a lead frame is not suited for use in a sensor that is needed to be small-sized. Further, in the event a lead frame large in the width size is used for a detection element formed with a plurality of electrode terminal sections that are small in the width size and positioned close to each other, one lead frame is brought into contact with all the plurality of electrode terminal sections, so that there is caused a possibility that a suitable electrical current path cannot be formed.

Over against such a problem, it will do to use a lead frame formed narrow in width and small in thickness. By using such a lead frame, it becomes possible to prevent the lead frame from applying an excessively large pressure to the detection element and make smaller the space for disposition of the lead frame. Further, by using a lead frame that is small in the width size, it becomes possible to prevent one lead frame from extending over a plurality of electrode terminal sections and contacting them.

However, a lead frame that is formed small in the width size or small in the thickness has a tendency to decrease in the rigidity.

In case under a condition where such a lead frame that is low in the rigidity is disposed in an element insertion hole of a separator, the detection element is inserted into the element insertion hole, the lead frame is liable to buckle due to the resistance to insertion at that time and be formed into an inadequate shape. When such deformation of the lead frame itself is caused, there arises a problem that suitable electrical connection between the lead frame and the electrode terminal section of the detection element cannot be attained or lead frames are brought into contact with each other to cause shortage.

Further, in case a sensor having a lead frame that is low in rigidity is, for example, subjected to a certain external force in actual use and its external shape is deformed, an inadequate external force is applied to the lead frame under the influence of the deformation of the sensor, thus possibly causing such a case where the relative positions of the lead frame and the detection element are changed. Namely, since the lead frame that is low in rigidity is liable to be deformed by an external force applied thereto, there is a possibility of the electrical connection between the lead frame and the electrode terminal section being unable to be maintained suitable when the lead frame is subjected to an inadequate external force to change the relative positions of the lead frame and the detection element.

SUMMARY OF THE INVENTION

The present invention has been made in view of the foregoing problems and has for its object to provide a sensor and a method of producing the same, which enables a lead frame to be hard to buckle even when an insertion resistance at the time of insertion of a detection element into an element insertion hole of a separator occurs and can maintain an electrical connection between the lead frame and an electrode terminal section of the detection element even when an inadequate external force is applied to the lead frame.

According to an aspect of the present invention, there is provided a sensor comprising a detection element in the form of an axially extending plate, having a front end side to face an object to be measured and formed with an electrode terminal section at a rear end side, a separator made of an insulating material and having an element insertion hole accommodating the rear end side of the detection element, and a metallic terminal member interposed between the detection element and an inner surface of the element insertion hole of the separator, wherein the metallic terminal member is formed from a metallic sheet material and includes an axially extending frame main body section, an element abutment section extending while being bent to change the direction of extension, from a front end of the frame main body section axially toward a rear end side of the frame main body section and contacting the electrode terminal section of the detection element thereby being electrically connected thereto to form a current path, and a frame locking section provided to a part of the frame main body and having a larger width than any other part of the frame main body section, and wherein the metallic terminal member is disposed within the separator so as to be put in a state of being engaged at the frame locking section with the separator.

The sensor is configured to include the metallic terminal member having the frame main body section and the element abutment section, and the metallic terminal member forms a current path for an external circuit, with the element abutment section contacting at least partially the electrode terminal section of the detection element.

In the sensor according to the present invention, the frame main body section of the metallic terminal member has the frame locking section having a width larger than any other part of the frame main body section, and the metallic terminal member is disposed within the separator, with the frame locking section being engaged with the separator.

By engaging, in this manner, the frame locking section formed at a portion of the frame main body section with the separator, it becomes possible to inhibit movement of the frame main body section axially toward a rear end side with respect to the separator or in the direction apart from the inner surface of the element insertion hole. Accordingly, since movement of the main body section can be suppressed even in the case an unsuitable external force is applied to the metallic terminal member, it becomes possible to prevent effectively a variation in the relative positions of the metallic terminal member and the detection element that are disposed within the separator.

Further, since the frame locking section is formed so as to be larger in the width than any other part of the frame main body section, the rigidity of the frame main body section can be retained even in the case the frame main body section is designed so as to be small in width (width size) and the locking force of the frame locking section with respect to the separator can be attained effectively. Further, by designing the frame locking section so as to be large in width, the frame locking section can, for example, be bent freely and therefore there is obtained such a merit that the design freedom of the frame locking section in engagement with the separator can be large.

In the meantime, the term "width (width size)" is herein used to indicate the size in the direction perpendicular to the axial direction and further to the direction of an intervening space between the element abutment section and the frame main body section.

Further, in the above-described sensor, it is preferable that the frame locking section has an extension portion that extends in the direction apart from the element abutment section and is bent at least once or more at an intermediate part thereof in a way as to change its direction of extension, the frame locking section being larger in width than the above-described other part of the frame main body section when the extension portion is developed in the width direction of the remaining portion of the frame main body section.

In the present invention, the frame locking section provided to a part of the frame main body section has the extension portion that extends in the direction apart from the element abutment section and is bent at least once or more at an intermediate part thereof. By constructing so that the frame locking section includes such an extension portion, it becomes possible to prevent the metallic terminal member (frame main body) itself from being formed with a portion that is excessively large in width even in the case the frame locking section is designed so as to be larger in width than any other part of the frame main body section. Accordingly, in case the metallic terminal member is disposed within the separator, a large space for disposition thereof is not necessitated, thus making it possible to make the sensor small-sized effectively.

Further, in any of the above-described sensors, it is preferable that the separator includes a locking groove for engagement with the frame locking section or a partition wall portion.

In engagement of the frame locking section with the separator, the frame locking section can be engaged with the separator more assuredly by providing the separator with the locking groove and accommodating the frame locking section within the locking groove thereby engaging the frame locking section with the locking groove.

Further, by disposing the partition wall portion between the element insertion hole and at least a part of the frame locking section, the frame locking section can be engaged with the separator easily.

In the meantime, it is preferable to form the above-described locking groove or/and the partition wall portion at the front end surface of the separator for ease of accommodation of the frame locking section of the metallic terminal member.

According to another aspect of the present invention, there is provided a sensor comprising a detection element in the form of an axially extending plate, having a front end side to face an object to be measured and formed with an electrode terminal section at a rear end side, a separator made of an insulating material and having an element insertion hole accommodating the rear end side of the detection element, and a metallic terminal member interposed between the detection element and an inner surface of the element insertion hole of the separator, wherein the metallic terminal member is formed from a metallic sheet material and having a frame main body section extending axially, an element abutment section extending while being bent to change the direction of extension, from a front end of the frame main body section axially toward a rear end side of the frame main body section and contacting the electrode terminal section of the detection element thereby being electrically connected thereto to form a current path, and a frame locking section provided to a part of the frame main body section, and wherein the separator has a locking groove at a front end surface thereof and the frame locking section is engaged with the locking groove.

The sensor according to another aspect of the present invention is also configured to include the metallic terminal member having the frame main body section and the element abutment section. To a part of the frame main body section is provided the frame locking section. By engaging the frame locking section with the separator, the metallic terminal member is disposed within the separator. By engaging the frame locking section provided to a part of the frame main body section with the separator, movement of the frame main body section can be suppressed even in the case an inadequate external force is applied to the metallic terminal member, and a variation in the relative positions of the metallic terminal member and the detection element that are disposed within the separator can be prevented effectively.

Further, in the sensor of this aspect of the invention, for engagement of the frame locking section with the separator, the separator has the locking groove at the front end surface thereof and the frame locking section is engaged with the locking groove.

By accommodating the frame locking section within the locking groove formed in the separator and thereby engaging them, the frame locking section can be engaged with the separator assuredly. Further, by forming the locking groove at the front end surface of the separator, the frame locking section can be accommodated within the locking groove easily.

According to a further aspect of the present invention, there is provided a sensor comprising a detection element in the form of an axially extending plate, having a front end side to face an object to be measured and formed with an electrode terminal section at a rear end side, a separator made of an insulating material and having an element insertion hole accommodating the rear end side of the detection element, and a metallic terminal member interposed between the detection element and an inner surface of the element insertion hole of the separator, wherein the metallic terminal member is formed from a metallic sheet material and having a frame main body section extending axially, an element abutment section extending while being bent to change the direction of extension, from a front end of the frame main body section axially toward a rear end side of the frame main body section and contacting the electrode terminal section of the detection element thereby being electrically connected thereto to form a current path, and a frame locking section having a first locking surface facing axially toward a rear end side of the frame main body section and a second locking surface facing in the direction of an intervening space between the frame main body section and the element abutment section and toward the element abutment section, and wherein the separator has a locking groove for disposition of the frame locking section and engages at an inner wall surface of the locking groove with the first locking surface and the second locking surface.

The sensor of this aspect of the invention is also configured so as to include the metallic terminal member having the frame main body section and the element abutment section. The metallic terminal member constitutes part of a current path for connection with an external circuit when at least a portion of the element abutment section is abuttingly engaged with the electrode terminal section.

In the sensor of this aspect of the invention, the metallic terminal member includes the frame locking section having the first locking surface and the second locking surface and is configured so that the frame locking section is disposed in the locking groove of the separator to engage the first locking surface and the second locking surface with the inner wall surface of the locking groove.

Engagement of the first locking surface of the frame locking section with the inner wall surface of the locking groove makes it possible to inhibit the frame main body section from moving axially toward the rear end side. Further, engagement of the second locking surface of the frame locking section with the inner wall surface of the locking groove makes it possible to inhibit the frame main body section from moving in the direction apart from the inner surface of the element insertion hole. Namely, even in the case an inadequate external force is applied to the metallic terminal member, movement of the frame main body section can be inhibited, thus making it possible to prevent the relative positions of the metallic terminal member and the detection element from being varied.

Thus, according to the present invention, in use of a metallic terminal member that is formed so as to be smaller in the width size or smaller in the thickness, it becomes possible to prevent the relative positions of the metallic terminal member and the detection element from being varied and maintain electrical connection between the metallic terminal member and the electrode terminal section suitably even in the case an inadequate external force is applied to the metallic terminal member.

In the meantime, the locking groove is preferably formed at the front end surface of the separator for easy accommodation of the frame locking section of the metallic terminal member therewithin.

Further, in the above-described sensor, the metallic terminal member is preferably configured so that a frame abutment portion of the element abutment section, which is positioned closer to a rear end of the frame main body section than an end portion of the element abutment section, which is connected to the front end of the frame main body section, is not abuttingly engaged with the frame main body section when the metallic terminal member is in a free state before being electrically connected to the electrode terminal section of the detection element, while being configured so that the frame abutment portion is abuttingly engaged with the frame main body section when the element abutment section is electrically connected to the electrode terminal section and resiliently deformed toward the frame main body section.

The metallic terminal member is configured so that when in a free state, the frame abutment portion of the element abutment section does not engage the frame main body section and the element abutment section is supported at one place (i.e., an end portion (hereinafter also referred to as "connection side end portion" connected to the front end of the frame main body section) by the frame main body section. For this reason, the metallic terminal member is configured, when in a state of the frame abutment portion of the element abutment section being not abuttingly engaged with the frame main body section, so as to be pressed against the electrode terminal section of the detection element by the stress caused by resilient deformation of a portion of the element abutment section, which is positioned adjacent the connection side end portion. The element abutment section continues resilient deformation toward the frame main body section to cause the frame abutment portion to abuttingly engage the frame main body section. By this, the element abutment section is supported at least at two places, i.e., at the connection side end portion and the frame abutment portion, by the frame main body section.

As described above, the metallic terminal member provided to the sensor of the present invention is configured so that the pressure that urges the metallic terminal member against the detection element varies depending upon whether or not the frame abutment portion of the element abutment section is abuttingly engaged with the frame main body section. More specifically, the metallic terminal member is configured so that the pressure that urges the metallic terminal member against the electrode terminal section of the detection element when the frame abutment portion of the element abutment section is abuttingly engaged with the frame main body section (two-point support condition) becomes larger as compared with that when the frame abutment portion of the element abutment section is not abuttingly engaged with the frame main body section (one-point support condition).

The element abutment section that is brought into the two-point support condition as described above when the sensor is completed produces a larger stress by resilient deformation thereof as compared with that when in one-support condition. Namely, the metallic terminal member can press the element abutment section against the electrode terminal section of the detection element with a larger stress and attain a good electrical condition between the metallic terminal member and the electrode terminal section of the detection element.

Further, in any of the sensors described above, it is preferable that the frame locking section includes a first connection portion extending from a front end side portion of the frame main body section in the direction apart from the element abutment section, a second connection portion extending from an end of the first connection portion axially toward the front end side, and a wide protrusion portion protruding from the second connection portion in the width direction of the second connection portion, wherein the first connection portion is formed with the above-described first locking surface, and the wide protrusion portion is formed with the second locking surface.

The first connection portion of the frame locking section provided to the sensor is configured so as to extend from the front end side portion of the frame main body section in the direction apart from the element abutment section. Since the direction of extension of the first connection portion is not parallel with the axial direction of the frame main body section, the first connection portion at least has a part (surface) that faces axially toward the rear end side of the frame main body section. Since that part can be used as the first locking surface, it becomes possible to inhibit the frame main body section (metallic terminal member) from moving axially toward the rear end side thereof.

Further, the second connection portion of the frame locking section is configured so as to extend from the end of the first connection part axially toward the front end, and the direction of extension of the second connection portion is not parallel with the direction of an intervening space between the frame main body section and the element abutment section. Thus, the second connection portion at least has a part (surface) that faces the element abutment section side. Since that part can be used as the second locking surface, it becomes possible to inhibit the frame main body section (metallic terminal member) from moving in the direction apart from the inner surface of the element insertion hole through engagement of at least a part of the second connection portion with the inner surface of the locking groove of the separator.

Namely, the metallic terminal member having the first connection portion and the second connection portion can prevent movement of the frame main body section even when an inadequate external force is applied thereto, thus making it possible to prevent the relative positions of the metallic terminal member and the detection element from being varied.

In the meantime, the wide protrusion portion can be formed, for example, so as to extend from a side surface of the second connection portion. Further, the wide protrusion part can be formed only at one side surface or each of the opposite side surfaces of the second connection portion. In the meantime, the term "width direction" is intended to indicate the direction perpendicular to the axial direction and further to the direction of an intervening space between the element abutment section and the frame main body section.

Further, in the above-described sensor, it is preferable that the wide protrusion or portions are formed so as to be asymmetrical about a center axis of the second connection portion.

As such sensors are enumerated an example in which the wide protrusion portion is formed only at one side surface of the second connection portion, an example in which the wide protrusion portions are formed at the respective side surfaces of the second connection portion and the width size (protrusion size) of one of the wide protrusion portions is formed so as to be larger as compared with that of the other, etc.

In the example of the sensor in which the wide protrusion portion is provided to only one side surface of the second connection portion, it becomes possible to inhibit movement of the frame main body section assuredly by the effect of abutting engagement of the wide protrusion portion with the locking groove of the separator even when an inadequate external force is applied to the metallic terminal member. Since the other side surface of the second connection portion is not formed with the wide protrusion portion, it will suffice that the locking groove of the separator has a region for abuttingly engagement with one wide protrusion portion. For this reason, as compared with the case where the second connection portion has the wide protrusion portions at the both side surfaces, a locking groove portion for engagement with the wide protrusion portion can be smaller in size and therefore there can be attained such an advantage that in the case where a plurality of metallic terminal members are arranged side by side the distance between the adjacent metallic terminal members can be made smaller.

Further, in an example of the sensor in which the second connection portion has the wide protrusion portions at the both side surfaces, it becomes possible to inhibit movement of the frame main body section assuredly by the effect of abutting engagement of the wide protrusion portions provided to the second connection portion with the locking groove of the separator even when an inadequate external force is applied to the metallic terminal member. Since the wide protrusion portion provided to one of the both side surfaces of the second connection portion is smaller in the protrusion size, it becomes possible to make the portion of the locking groove of the separator for abutting engagement with the wide protrusion portion smaller in size, and therefore there can be attained such an advantage that in the case where a plurality of metallic terminal members are arranged side by side the distance between the adjacent metallic terminal members can be made smaller.

By making smaller the space for disposition of the metallic terminal members, the density of the number of the metallic terminal members disposed per a unit length can be made higher and therefore the number of the metallic terminal members that can be disposed in the element insertion hole of the same size can be increased. For this reason, in case the detection element has a number of electrode terminal sections, the metallic terminal members can be connected to the respective electrode terminal sections assuredly.

In the meantime, the term "width size (protrusion size)" of the wide protrusion portion is intended to indicate the size from the end of the wide protrusion portion for connection with the second connection portion to the end positioned at the outer side with respect to the width direction of the second connection portion.

Further, in any of the above-described sensors, it is preferable that the frame locking section includes a first extension portion extending from a front end side portion of the frame main body section in the direction apart from the element abutment section and a second extension portion extending from an end of the first extension portion on the side remoter from the element abutment section in parallel with the frame main body section, at least one of the first extension portion and the second extension portion is formed with the first locking surface and the second extension portion is formed with the second locking surface.

The first extension portion of the frame locking section provided to the sensor extends from the front end side part of the frame main body section in the direction apart from the element abutment section and the direction of extension is not parallel with the axial direction of the frame main body section, so that the first extension portion has at least a part (surface) that faces axially toward the rear end side of the frame main body section. Since that part can be used as the first locking surface, it becomes possible to inhibit the frame main body section (metallic terminal member) from moving axially toward the rear end side through engagement of at least a part of the first connection portion with the inner wall surface of the locking groove of the separator.

Further, since the second extension portion of the frame locking section extends parallel with the frame main body section and the direction of extension is not parallel with the direction of an intervening space between the frame main body section and the element abutment section, the second extension portion has at least a part that faces the element abutment section side. Since that part can be used as the second locking surface, it becomes possible to inhibit the frame main body section (metallic terminal member) from moving in the direction apart from the inner surface of the element insertion hole through engagement of at least a part of the second connection portion with the inner wall surface of the locking groove of the separator.

Namely, the metallic terminal member provided with the frame locking section having the first extension portion and the second extension portion can inhibit movement of the frame main body section and prevent the relative positions of the metallic terminal member itself and the detection element from being varied even when subjected to an inadequate external force.

In the meantime, the direction of extension of the second extension portion will suffice if it enables the second extension portion to have at least a part (surface) that faces in the direction of an intervening space between the frame main body section and the element abutment section and toward the element abutment section, and is not limited to a particular direction. For example, the second extension portion may be disposed so as to extend from the axial front end side or the axial rear end side of the frame main body section.

Further, in the above-described sensors, it is preferable that at least two of the locking sections are provided so as to extend from different places of a front end side portion of the frame main body section.

By using the metallic terminal member having at least two frame locking sections, it becomes possible to increase the area of an engagement portion at which the frame locking sections are engaged with the separator (the inner wall surface of the locking groove), thus making it possible to inhibit movement of the frame main body section more assuredly and prevent a variation in the relative positions of the metallic terminal member and the detection element more assuredly even when an inadequate external force applied to the metallic terminal member becomes larger.

As an example of a metallic terminal member having two frame locking sections can be enumerated, for example, a metallic terminal member configured to have frame locking sections that extend from the end portions opposed in the width direction of the frame main body section. Further, the frame locking section can be formed so as to have a nearly L-shaped cross section with respect to a sectional plane perpendicular to the axial direction and thereby can have the first extension portion and the second extension portion. Further, in the metallic terminal member having a plurality of frame locking sections, it is not necessitated to limit the extension directions of the second extension portions of each frame locking section to the same direction but the second extension portions of each frame locking section may be formed so as to extend in the different directions in accordance with the shape of the locking groove of the separator.

Further, in any of the above-described sensors, it is preferable that the frame locking section includes a first frame connection portion extending from a front end side portion of the frame main body section in the direction apart from the element abutment section, a second frame connection portion extending from an end of the first connection portion on the side remoter from the element abutment section, axially toward the rear end side of the frame main body section, and a third frame connection portion extending from the end of the second connection portion on the side opposite to the side for connection with the first frame connection portion so as to be connected to the element abutment section, wherein the first frame connection portion is formed with the first locking surface and the second frame connection portion is formed with the second locking surface.

Since the first frame connection portion of the frame locking section provided to the sensor is configured so as to extend from the front end side portion of the frame main body section in the direction apart from the element abutment section and the direction of extension thereof is not parallel with the axial direction of the frame main body section, the first frame connection portion has at least a part (surface) that faces axially toward the rear end side of the frame main body section. Since that part can be used as a first locking surface, movement of the frame main body section (metallic terminal member) axially toward the rear end side can be inhibited through engagement of at least a part of the first connection portion with the inner wall surface of the locking groove of the separator.

Further, since the second frame connection portion of the frame locking section is configured so as to extend from an end of the first frame connection portion axially toward the rear end side and the direction of extension thereof is not parallel with the direction of an intervening space between the frame main body section and the element abutment section, the second frame connection portion has at least a part (surface) that faces the element abutment side. Since that part can be used as second locking surface, movement of the frame main body section (metallic terminal member) in the direction apart from the inner surface of the element insertion hole can be inhibited through engagement of at least a part of the second connection portion with the inner wall surface of the locking groove of the separator.

Namely, the metallic terminal member provided with the frame locking section having the first frame locking section and the second frame locking section can inhibit movement of the frame main body section even when an inadequate external force is applied thereto and therefore can prevent the relative positions of the metallic terminal member itself and the detection element from being varied.

Further, in any of the above-described sensors, it is preferable that the detection element has a plural number of the electrode terminal sections, a plural number of the metallic terminal members are provided in accordance with the number of the electrode terminal sections and connected to the different lead wires, respectively, and the element insertion hole of the separator is formed so as to extend axially throughout thereof and sized so as to enable all of the lead wires to be inserted thereinto.

Namely, the separator does not have one lead wire insertion hole for each lead wire but is configured so as to employ such an element insertion hole that is sized to enable all of the lead wires to be inserted thereinto as a lead wire insertion hole. In this instance, since the element insertion hole has a larger opening sectional area as compared with the lead wire insertion hole for each lead wire, it becomes possible to attain a larger spacing interval between the lead wire and the inner surface of the element insertion hole. By this, it becomes difficult for the lead wire to be caught by the inner wall of the element insertion hole at the time of the work for insertion, thus making it possible to prevent a coating material from being cut off by the lead wire at the time of the work for lead wire insertion and reduce the complexity of the work for insertion of the lead wire into the element insertion hole of the separator.

According to a further aspect of the invention, there is provided a method of producing a sensor including a detection element in the form of an axially extending plate, having a front end side to face an object to be measured and formed with an electrode terminal section at a rear end side, a separator made of an insulating material and having an element insertion hole accommodating the rear end side of the detection element, and a metallic terminal member interposed between the detection element and an inner surface of the element insertion hole of the separator, wherein the metallic terminal member is formed from a metallic sheet material and having a frame main body section extending axially, an element abutment section extending while being bent to change the direction of extension from a front end of the frame main body section axially toward a rear end side of the frame main body section and contacting the electrode terminal section of the detection element thereby being electrically connected thereto to form a current path, and a frame locking section having a first locking surface facing axially toward a rear end side of the frame main body and a second locking surface facing in the direction of an intervening space between the frame main body section and the element abutment section and toward the element abutment section, wherein the separator has a locking groove for disposition of the frame locking section, the method comprising a first step of disposing at least the element abutment section of the metallic terminal member within the element insertion hole of the separator and disposing the frame locking section within the locking groove, thereby engaging the first locking surface and the second locking surface with the inner wall surface of the locking groove, a second step of disposing the rear end side of the detection element, at which the detection element is formed with the electrode terminal section, at a front end side of the separator, and a third step of inserting the rear end side of the detection element into the element insertion hole of the separator and bringing the electrode terminal section of the detection element and the metallic terminal member into contact with each other.

In the sensor production method, the frame locking section of the metallic terminal member is disposed in the locking groove of the separator to engage the first locking surface and the second locking surface with the inner surface of the locking groove. By engaging the first locking surface and the second locking surface with the inner surface of the locking groove in this manner, it becomes possible to restrict movement of the frame main body section in the direction of the axial rear end side. Further, by engaging the second locking surface of the frame locking section with the inner surface of the locking groove, it becomes possible to restrict movement of the frame main body section in the direction apart from the inner surface of the element insertion hole.

For this reason, in case of insertion of the detection element into the element insertion hole of the separator in the third step, the first locking surface and the second locking surface are engaged with the inner surface of the locking groove even when an external force due to a friction force (resistance to insertion) caused between the detection element and the metallic terminal member (specifically, element abutment section) is applied to the metallic terminal member, thus making it possible to inhibit movement of the frame main body section (metallic terminal member).

Thus, by the sensor production method of the present invention, the relative positions of the metallic terminal member and the electrode terminal section of the detection can be prevented from becoming inadequate at the time of the work for inserting the detection element into the separator, and the metallic terminal member and the electrode terminal section of the detection element can be electrically connected assuredly. Further, since movement of the metallic terminal member at the time of production of the sensor is restricted through engagement of the frame locking section with the locking groove, buckling of the metallic terminal member is hard to be caused, thus making it possible to prevent the metallic terminal member and the electrode terminal section of the detection element from being disabled to be electrically connected.

Further, in the above-described sensor production method, it is preferable that the metallic terminal member is configured so that the frame abutment portion of the element abutment section, which is positioned closer to the rear end than the end portion of the element abutment section for connection with the front end of the frame main body section, is not abuttingly engaged with the frame main body section when the element abutment section is in a free state before being electrically connected to the electrode terminal section of the detection element, while being configured so that the frame abutment portion is abuttingly engaged with the frame main body section when the metallic terminal member is electrically connected to the electrode terminal section to cause the element abutment section to resiliently deform toward the frame main body section, wherein it is preferable that the first step includes disposing the metallic terminal member in a state of not receiving any external force within the element insertion hole of the separator and the third step includes inserting the detection element into the element insertion hole while pushing the detection element against the element abutment section, thereby resiliently deforming the element abutment section toward the frame main body section and abuttingly engaging the frame abutment portion of the element abutment section with the frame main body section.

The metallic terminal member is configured so as to produce a variable pressure for pressing the metallic terminal member against the detection element depending upon whether or not the frame abutment portion of the element abutment section is abuttingly engaged with the frame main body section. More specifically, the metallic terminal member is configured so as to produce a larger pressure for pressing the metallic terminal member itself against the electrode terminal section of the detection element when the frame abutment portion of the element abutment section is not abuttingly engaged with the frame main body section (one-point support state) as compared with that produced thereby when the frame abutment portion of the element abutment section is abuttingly engaged with the frame main body section (two-point support state).

By this, in case of assembly of the metallic terminal member and the detection element in a sensor production process, the element abutment section of the metallic terminal member is pressed against the electrode terminal section of the detection element with a relatively smaller force in the first half of the assembly work, thus making it possible to inhibit an excessively large pressure from being applied to the detection element and causing breakage thereof.

BRIEF DESCRIPTION OF THE DRAWINGS

FIG. 3 is a perspective view depicting an external appearance of a lead frame 10 including FIG. 3A showing a first lead frame 11 and FIG. 3B showing a second lead frame 211;

FIG. 11 is a perspective view including FIG. 11A and FIG. 11B showing external appearances of a fifth lead frame 351 and sixth lead frame 353, respectively;

DETAILED DESCRIPTION OF THE INVENTION

An embodiment of the present invention will be described hereinafter by reference to drawings.

In the meantime, according to this embodiment will be described a kind of gas sensor, specifically a wide-range air/fuel ratio sensor 2 (hereinafter also referred to as air/fuel ratio sensor 2) composed of a detection element (gas sensor element) for detecting a particular gas which is an object to be measured and contained in an exhaust gas, for use in an air/fuel ratio feedback control in automotive or other various kinds of internal combustion engines.

Figure 1:
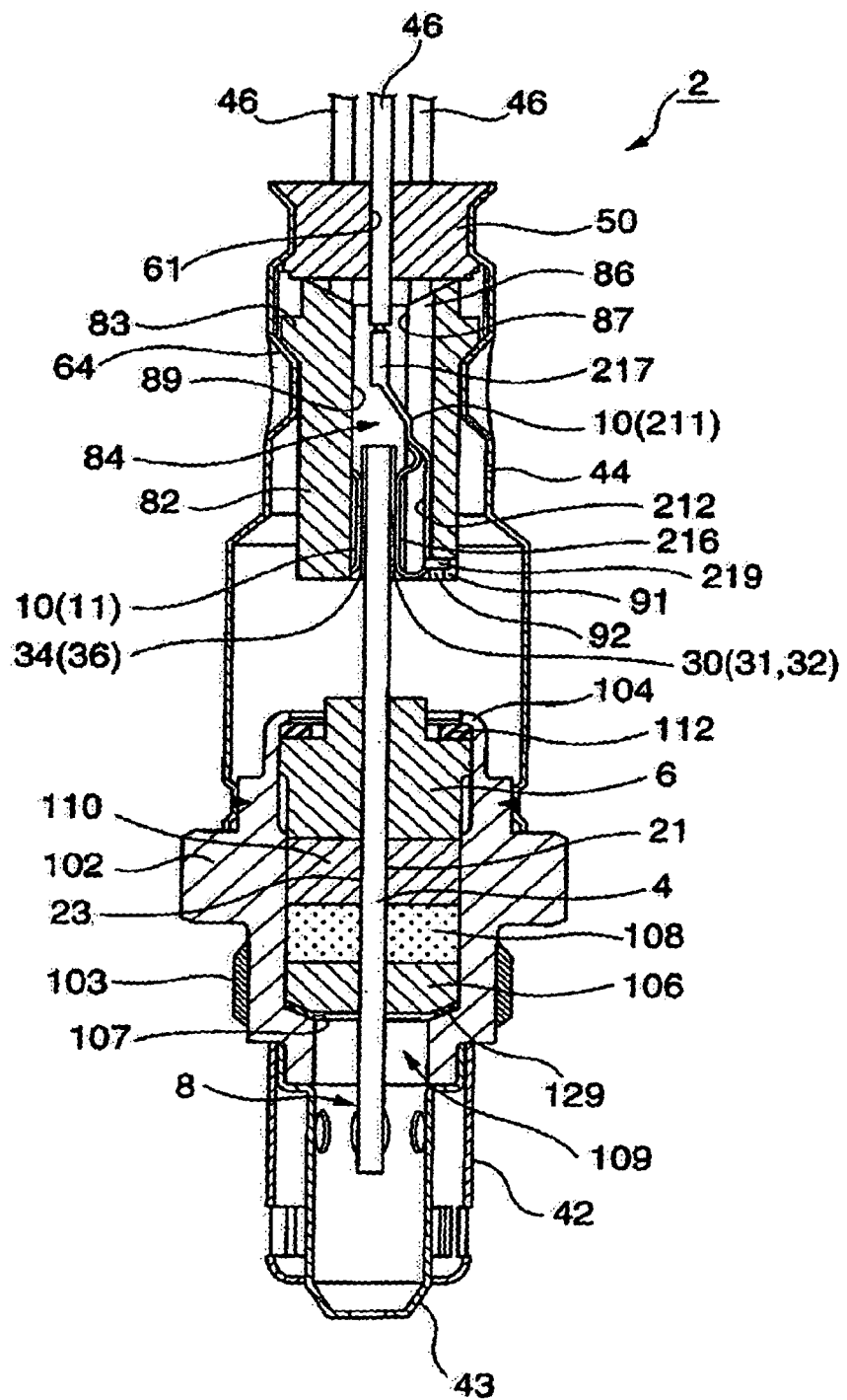
FIG. 1 is a sectional view showing an overall structure of a wide-range air/fuel ratio sensor according to an embodiment.

FIG. 1 is a sectional view showing an overall structure of the air/fuel ratio sensor 2 according to an embodiment of the present invention.

The air/fuel ratio sensor 2 includes a detection element 4 in the form of a plate extending in an axial direction (vertical direction in the drawing), a tubular metallic housing 102 accommodating the detection element 4 in a way as to allow a front end portion of the detection element 4 to protrude therefrom, a ceramic sleeve 6 disposed between the detection element 4 and the metallic housing 102, and a separator 82 made of alumina and disposed in a way as to surround a rear end portion of the detection element 4.

Figure 2:
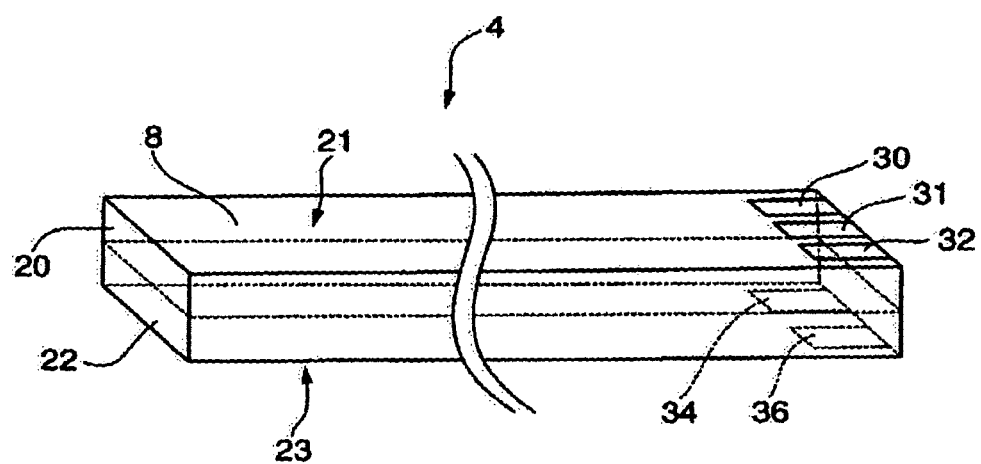
FIG. 2 is a perspective view depicting a schematic structure of a detection element.

The detection element 4 is in the form of an axially extending plate and formed at a front end side (lower side in the figure) to face a gas that is an object to be measured, with a detection section 8 covered by a protection layer and at a first plate surface 21 and a second plate surface 23 of outer surfaces of a rear end side (upper side in the figure), which first and second plate surfaces have a relation between a front side and a rear side, with electrode terminal sections 30, 31, 32, 34 and 36 (refer to FIG. 2). Five lead frames (metallic terminal members) 10 are disposed between the detection element 4 and the separator 82 and electrically connected to the electrode terminal sections 30, 31, 32, 34 and 36, respectively. Further, the lead frames 10 are electrically connected at the rear end sides thereof to lead wires 46 that are disposed inside the sensor through movement from the outside and constitute electrical paths for current flowing between an external circuit to which the lead wires 46 are connected and the electrode terminal sections 30, 31, 32, 34 and 36.

The metallic housing 102 has at an outside surface a threaded section 103 for fixation to an exhaust pipe and is formed into a nearly tubular shape having inside thereof a through hole extending axially therethrough. Further, the metallic housing 102 is configured so as to allow the detection section 8 to protrude from the front end side and hold therewithin the detection element 4 in a way as to allow the electrode terminal sections 30, 31, 32, 34 and 36 to protrude from the rear end side.

To the front end side (lower side in FIG. 1) outer periphery of the metallic housing 102 is attached by welding or the like an outer protector 42 and inner protector 43 which are made of metal (for example, stainless steel or the like) to constitute a dual-wall and have a plurality of holes.

Further, a separator 82 is disposed around the rear end side (upper side in FIG. 1) of the detection element 4, which protrudes from a rear end portion 104 of the metallic housing 102 and accommodates the electrode terminal sections 30, 31, 32, 34 and 36 within an insertion hole 84.

To the rear end side outer periphery of the metallic housing 102 is fixedly attached an outer tube 44. At the rear end side (upper side in FIG. 1) opening portion of the outer tube 44 is disposed a grommet 50, and lead wires 46 are inserted into lead wire insertion holes 61 of the grommet 50.

Within a through hole 109 of the metallic housing 102 are placed one upon another an annular ceramic holder 106, a power filling layer 108 (hereinafter also referred to as talcum ring 108), an auxiliary sleeve 110 and a ceramic sleeve 6 in this order from the front end side to the rear end side in a way as to surround the circumferential periphery of the detection element 4. These laminated layers are fixedly held between a shoulder portion 107 and a rear end portion 104 by caulking by way of packing 129 and a caulking ring 112.

In this connection, a perspective view of the schematic structure of the detection element 4 is shown in FIG. 2. In the meantime, in FIG. 2, an axially intermediate portion of the detection element 4 is omitted.

The detection element 4 includes an element section 20 formed into an axially (in the horizontal direction in FIG. 2) extending plate shape and a heater 22 formed into a similar axially extending plate shape extending, which are placed one upon another to allow the detection element to be formed into a plate shape having a rectangular cross section. In the meantime, since the detection element 4 used as the air/fuel ratio sensor 2 is of the type known in the art, the detailed description of the inside structure, etc. are omitted but the schematic structure thereof is as follows.

Firstly, the element section 20 consists of an oxygen concentration cell including porous electrodes formed on the opposite sides of a solid electrolytic substrate, an oxygen pump cell including porous electrodes similarly formed on the opposite sides of a solid electrolytic substrate, and a spacer placed between the cells for forming a hollow gas measurement chamber. The solid electrolytic substrate is made of a solid solution of zirconia and yttria as a stabilizer, and the porous electrode is made of a material containing Pt as a major component. Further, the spacer that forms the gas measurement chamber is made of a material containing alumina as a major component, and one of the porous electrodes of the oxygen concentration cell and one of the porous electrodes of the oxygen pump cell are disposed so as to be exposed to the hollow measurement gas chamber. In the meantime, the measurement gas chamber is formed so as to be positioned at the front end side of the element section 20, and a portion of the element section, at which the measurement gas chamber is formed, corresponds to the detection section 8.

Then, the heater 22 is formed so as to have a heating resistor pattern that is made of a material containing Pt as a major component and interposed between insulating substrates made of alumina as a major component.

The element section 20 and the heater 22 are connected to each other by interposing therebetween a ceramic layer (e.g., zirconia system ceramic or alumina system ceramic). Further, on at least the surface of the electrodes of the detection element 4, which is exposed to an object to be measured (in this embodiment, exhaust gas) is formed a protection layer (not shown) made of porous ceramic for protection from poisoning. In the meantime, in this embodiment, the protection layer covers all the front end side surface of the detection element, which includes the surface of the electrode to be exposed to the exhaust gas.

Such a detection element 4, as shown in FIG. 2, is formed with three electrode terminal sections 31, 32, 33 at the rear end side (the right-hand side in FIG. 2) of the first plate surface 21 and two electrode terminal sections 34, 36 at the rear end side of the second plate surface 23. The electrode terminal sections 30, 31, 32 are formed at the element section 20, one of which electrode terminal sections is electrically connected, in the manner of common use, to one of the porous electrodes of the oxygen concentration cell that is exposed to the inside of the measurement gas chamber and one of the porous electrodes of the oxygen pump cell. Further, remaining two of the terminal electrodes 30, 31, 32 are electrically connected to the other of the porous electrodes of the oxygen concentration cell and the other of the porous electrodes of the oxygen pump cell. Further, the electrode terminal sections 34, 36 are formed at the heater 22 and connected to the opposite ends of the heating resistor pattern by way of a via (not shown) extending crosswise in the thickness direction of the heater 22, respectively.

Figure 4:
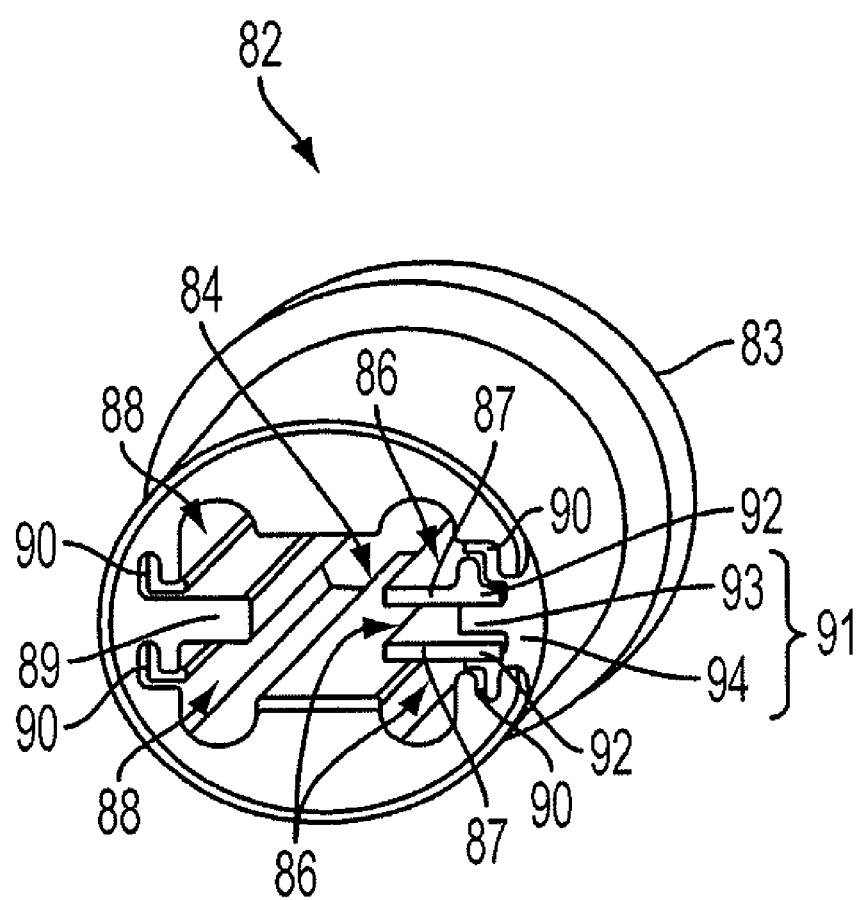
FIG. 4 is a perspective view of an external appearance of a separator.

Then, the separator will be described. FIG. 4 is a perspective view showing the external appearance of the separator 82 when observed from the front end side thereof.

As shown in FIG. 4, the separator 82 is made of alumina and formed into a tubular shape so as to have an insertion hole 84 extending axially therethrough while being provided with a flange portion 83 protruding radially outward from an external surface thereof. The separator 82 is disposed inside the outer tube 44 by being abuttingly engaging at the flange portion 83 with an outer tube side support portion 64 of the outer tube 44. In the meantime, the outer tube side support portion 64 is formed so as to protrude inward of the outer tube 44 (refer to FIG. 1).

At the inner wall surface of the insertion hole 84, which faces the first plate surface 21 (not shown), and at two places thereof are formed first rib portions 87 that protrude inward. The first rib portions 87 are provided so as to serve as lead frame boundary portions inside the insertion hole, which form boundaries of three first frame disposition grooves 86 for disposing three lead frames 10 in a state of being electrically insulated from each other. The three first frame disposition grooves 86 are formed at the first plate surface 21 of the detection element 4 and at the positions corresponding to the electrode terminal sections 30, 31, 32, respectively.

Further, at the inner wall surface of the insertion hole 84, which faces the second plate surface 23 (not shown) of the detection element 4, and at one place thereof is formed a second rib portion 89 that protrudes inward. The second rib portion 89 is provided to serve as a lead frame boundary portion inside the insertion hole, which forms a boundary of two second frame disposition grooves 88 for disposing the two lead frames 10 in a state of being electrically insulated from each other. The second disposition grooves 88 are formed at the second plate surface 23 of the detection element 4 and at the positions corresponding to the electrode terminal sections 34, 36.

The first rib portions 87 and second rib portion 89 have a function of preventing the lead frames 10 disposed in the adjacent frame disposition grooves from contacting each other and can prevent the electrical path from becoming defective by preventing the lead frames 10 from being electrically connected to each other.

Further, the separator 82 has at the front end surface thereof (this side surface in the figure) first locking grooves 90 and a second locking groove 91 that are formed so as to be joined to the front end side opening portion of the insertion hole 84.

The first locking grooves 90 are formed into a nearly L-shape when observed from the front end side and configured so as to dispose therewithin a first frame locking section 19 of the lead frame 10, which will be described later. In the meantime, the first locking grooves 90 are formed at two places where they are connected to two of the three first frame disposition grooves 86, which are formed at the opposite sides and at two places where they are connected to the two second frame disposition grooves 88.

The second locking groove 91 consists of a narrower groove portion 93 formed between two protrusion portions 92 and a wider groove portion 94 formed at a portion of the separator 82, which is positioned at a radially outer side of the narrower groove portion 93, and is configured so as to dispose therewithin a second frame locking section 219 of the lead frame 10, which will be described later. In the meantime, the protrusion portion 92 is formed so as to be continuous from an end of the first rib portion 87. Further, the second locking groove 91 is formed at one place where it is connected to one first frame disposition groove 86 that is formed in the middle of the three first frame disposition grooves 86.

Further, the separator 82 has a partition wall portion. The partition wall portion is formed between the first locking groove 90 and the insertion hole 84. At the time of installation of the lead frame 10, the partition wall is positioned between the first frame locking section 19 that is inserted into the first locking groove 90 and the element insertion hole to perform a function of preventing falling off of the first frame locking section 19.

Then, the lead frame 10 will be described. FIG. 3 is a perspective view showing the external appearance of the lead frame 10. In the meantime, the air/fuel ratio sensor 2 of this embodiment is configured to include two kinds of lead frames 10 that are different in the shape of the frame locking section (the first lead frame 11 on the left-hand side of FIG. 3 and the second lead frame 211 on the right-hand). Further, the lead frame 10 is made of a known material (e.g., inconel, stainless steel or the like) that can maintain the resiliency (springing resilience) even when exposed to a high temperature repeatedly.

First, the first lead frame 11 will be described.

The first lead frame 11 includes a frame main body section 12 formed from an axially extending plate, an element abutment section 16 extending while being bent, from a front end of the frame main body section 12 so as to be disposed between the frame main body section 12 and the detection element 4 and having a portion at which it is abuttingly engaged with the electrode terminal section of the detection element 4, and a lead wire connection section 17 electrically connected with a lead wire 46.

The frame main body section 12 has nearly at an axially central position a curved portion 13 and is configured so that a front end side portion closer to the front end than the curved portion 13 and a rear end side portion closer to the rear end than the curved portion 13 are different in the position with respect the plate surface thickness direction. The surface of the curved portion 13, that faces the frame abutment portion 15 constitutes an inclined surface that faces the front end side and has a function of inhibiting the frame abutment portion 15 from moving axially toward the rear end side or radially outward at the time of abutting engagement with the frame abutment portion. Further, the frame main body section 12 is formed so as to be 1.1 mm in the width size W1 and 0.2 mm in the thickness at the plate surface of the front end side portion closer to the front end than the central position.

Herein, the "width size" is intended to indicate the size perpendicular to the axial direction and to the direction in which the element abutment section 16 and the frame main body section 12 are spaced from each other. Further, the lead frames 10 (first lead frame 11 and second lead frame 211) are formed so as to be smaller in the width size and in the thickness as compared with the conventional lead frame.

The first lead frame 11 has a first frame locking section 19 that is formed able to be disposed in the first locking groove 90 of the separator 82. The first frame locking section 19 is extended from a side surface of a front end side portion of the frame main body section 12 in the direction perpendicular to the plate surface and bent so as to have a portion parallel with the plate surface of the frame main body section 12. Namely, the first frame locking section 19 has a larger width (total width) than the remaining portion of the frame main body section 12 when developed so as to extend in the width direction of the remaining portion.

The first frame locking section 19 has a first extension portion 131 extending from a side surface of a front end side portion of the frame main body section 12 in the direction perpendicular to the plate surface and a second extension portion 133 extending from an end of the first extension portion 131, which is opposite to a connection side for connection with the frame main body section 12, in parallel with the frame main body section 12. Of the extension portions, the first extension portion 131 extends from the front end side portion of the frame main body section 12 in the direction apart from the element abutment section 16.

The first extension portion 131 and the second extension portion 133 of the first frame locking section 19 have a first locking surface 135 that faces axially toward the rear end side, and the second extension portion 133 has a second locking surface 137 that faces in the direction of an intervening space between the frame main body section 12 and the element abutment section 16 and toward the element abutment section 16.

The element abutment section 16 is configured so as to extend while being bent radially inward to change the direction of extension, from a front end of the frame main body section 12 axially toward the rear end side. The element abutment section 16 includes a connection side end portion 14 connected to the front end of the frame main body section 12 and a frame abutment portion 15 that is positioned closer to the rear end than the connection side end portion 14 and put in a state of being spaced apart from the frame main body section 12 when the first lead frame 11 itself is in a free state.

Herein, the element abutment section 16 is formed so as to be 1.1 mm in the width side of the plate surface and 0.2 mm in the thickness. Further, element abutment section 16 is formed into a circular arc shape and curved so that the distance between the axially central portion and the frame main body section 12 is larger as compared with that between the frame abutment portion 15 and the frame main body section 12 and a convex side curved surface of the circular arc shape is abuttingly engaged with the detection element 4.

In the meantime, when an external force is applied to the element abutment section 16 (specifically, an external force from the element abutment section 16 toward the frame main body section 12 is applied), the frame abutment portion 15 is resiliently deformed toward the frame main body section 12, and finally the frame abutment portion 15 is abuttingly engaged with the curved portion 13 of the frame main body section 12.

Further, the first lead frame 11 is configured so that when there is no external force applied thereto and the connection side end section 14 (the element abutment section itself) is not resiliently deformed, the distance between the abutment portion 15 of the element abutment section 16 and the frame main body section 12 is smaller than the depth of the first frame disposition groove 86 and the second frame disposition groove 88 of the separator 82.

In the meantime, the first lead frame 11 is configured so that in case the element abutment section 16 in a state of being resiliently deformed toward the frame main body section 12 is held between the detection element 4 and the separator 82, the abutment portion 15 of the element abutment section 16 is brought into contact with the curved portion 13 of the frame main body section 12 and at least a portion of the element abutment section 16 protrudes from the first frame disposition groove 86 and the second frame disposition groove 88 to contact an electrode terminal section of the detection element 4.

Then, the second lead frame 211 will be described.

The second lead frame main body section 212 is formed so that a front end side portion closer to the front end than a portion around a curved portion 213 is 0.8 mm in the plate surface width W2 and 0.2 mm in the plate thickness and substantially similar in the sectional shape with respect to a plane parallel to the axial direction and perpendicular to the plate surface, to the frame main body section 12 though different in the width of a lateral surface from the frame main body section 12 of the first lead frame 11.

The second element abutment section 216 is formed so as to be 0.8 mm in the plate surface width W2 and 0.2 mm in the plate thickness and substantially similar in the circular arc sectional shape with respect to a plane parallel to the axial direction, to the element abutment section 16, and has a second connection side end portion 214 corresponding to the connection side end portion 14 and a second frame abutment portion 215 corresponding to the frame abutment portion 15.

Further, the second lead frame 211 has at a portion of the second frame main body section 212 two second frame locking sections 219 that can be disposed in the second locking grooves 91 of the separator 82. The second locking sections 219 are configured so as to extend from the second main body section 212 in the direction perpendicular to the plate surface thereof and be bent outward to have portions parallel to the plate surface of the second frame main body section 212 thereby being nearly L-shaped in section. Namely, the second frame locking section 219, when developed in the width direction of a remaining portion of the second frame main body section 212, has a wider width than that of the remaining portion.

The second locking section 219 has a third extension portion 231 extending from the front end side portion of the second frame main body section 212 in the direction perpendicular to the plate surface thereof and a fourth extension portion 233 extending from the end of the third extension portion 231, which is positioned at the side opposite to the connection side for connection with the second frame main body section 212, in parallel with the second frame main body section 212. Of the extension portions, the third extension portion 231 extends from the front end side portion of the second frame main body section 212 in the direction of an intervening space between the second frame main body section 212 and the second element abutment section 216 and in the direction apart from the second element abutment section 216. Further, the two second frame locking sections 219 are configured so that the fourth extension portions 233 extend in the opposite directions.

Of the second frame locking section, the third extension portion 231 and the fourth extension portion 233 have a third locking surface 235 facing axially toward the rear end side of the second frame main body section 212, and the fourth extension portion 233 has a fourth locking surface 237 facing the second element abutment section 216.

Further, the second lead frame 211 has a second lead wire connection section 217 which is formed into a similar shape to the lead wire connection section 17 of the first lead frame 11 and in a manner as to be connected to the rear end of the second lead frame main body section 212.

Of the lead frames 10 configured in this manner, the four first lead frames 11 and one second lead frame 211 are inserted into the insertion hole 84 of the separator 82 so as to be put in a state of being insulated from each other by the first rib portions 87 and the second rib portions 89. In this instance, the four first lead frames 11 are disposed in the two first frame disposition grooves 86 corresponding to the electrode terminal sections 30, 32 of the detection element 4 and in the two frame disposition grooves 88 corresponding to the two second frame disposition grooves 88 corresponding to the electrode terminal sections 34, 36. The second lead frame 211 is disposed in the first frame disposition groove 86 corresponding to the electrode terminal section 31 of the detection element 4.

Figure 5:
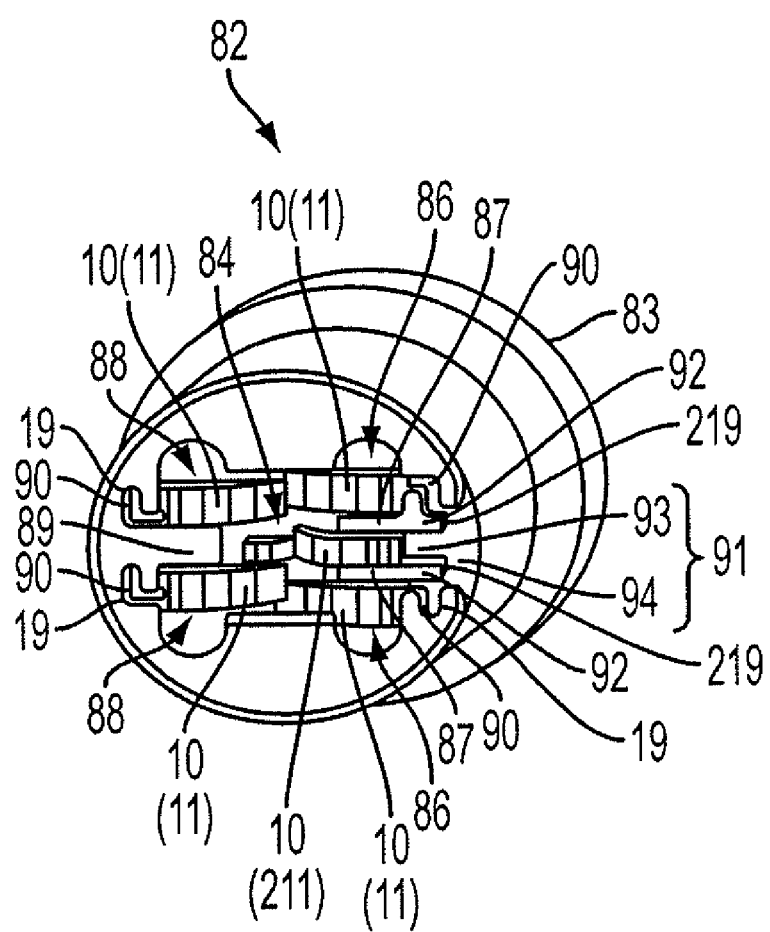
FIG. 5 is a perspective view of a separator in a state where a lead frame is disposed in an insertion hole.

FIG. 5 is a perspective view of the separator 82 insertion hole 84 in the state in which the lead frame 10 is inserted into the insertion hole 84.

As shown in FIG. 5, in case the first lead frame 11 is disposed in the insertion hole 84, the first frame locking section 19 of the first lead frame 11 is disposed in the first locking groove 90 of the separator 82. As a result, the first locking surface 135 of the first frame locking section 19 (refer to FIG. 3) and the second locking surface 137 (refer to FIG. 3) are put into a condition of being engaged with the inner wall surface of the first locking groove 90.

Further, in case the second lead frame 211 is disposed in the insertion hole 84 of the second lead frame 211, the second frame locking section 219 of the second lead frame 211 is disposed in the second locking groove 91 of the separator 82. As a result, the third locking surface 235 of the second frame locking section 219 (refer to FIG. 3) and the fourth locking surface 237 (refer to FIG. 3) are put into a condition of being engaged with the inner wall surface of the second locking groove 91.

In the meantime, the lead frame 10 is disposed in the insertion hole 84 through insertion into the insertion hole 84 of the separator together with the lead wire 46 after the lead wire 46 is connected to the lead wire connection section 17 (second lead wire connection section 217).

By inserting the detection element 4 into the insertion hole 84 of the separator 84 in a state of disposing therein the lead frames 10 as described above, the element abutment sections 16 (second element abutment sections 216) can be abuttingly engaged and electrically connected with the electrode terminal sections 30, 31, 32, 34, 36 of the detection element 4.

Then, the assembly work for inserting the detection element 4 into the insertion hole 84 in a state of disposing therein the lead frames 10 thereby assembling the detecting element 4, the lead frame 10 and the separator 82 into a unit will be described.

Figure 6:
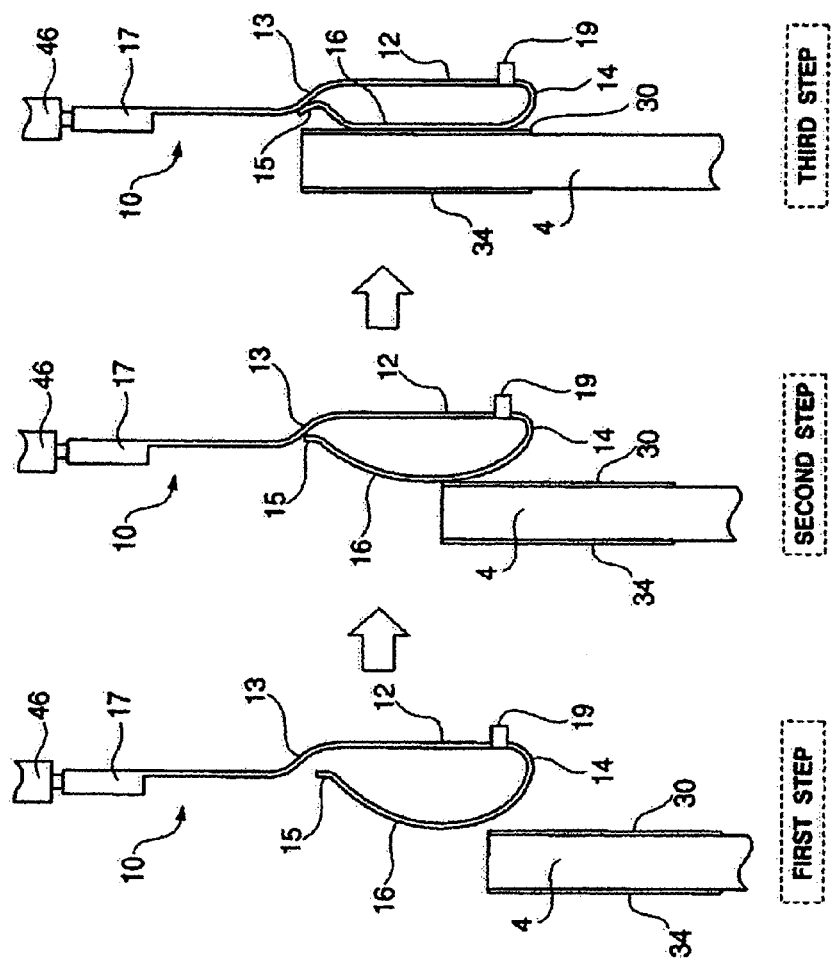
FIG. 6 is a view for illustrating states of deformation of the lead frame within the insertion hole at the time of a work for inserting the detection element into the separator.

FIG. 6 illustrates the states of deformation of the lead frame 10 within the insertion hole 84 during the work for inserting the detection element 4 into the insertion hole 84 of the separator 82. In the meantime, in FIG. 6, one lead frame 10 and the detection element 4 are shown and the separator 82 is omitted for brevity.

First, at the first step immediately after the beginning of the assembly work, the detection element 4 is disposed at the front end side of the separator 82 and thereafter the detection element 4 is moved to the front end side opening portion of the insertion hole 84 while at the same time the detection element 4 is abuttingly engaged with the element abutment section 16 of the lead frame 10.

Then, in the second step, the detection element 4 is pushed against the element abutment section 16 of the lead frame 10 to apply thereto an external force thereby performing a work for resiliently deforming the portion around the connection side end portion 14 (namely, the element abutment section 16 is resiliently deformed toward the frame main body section 12) and making the frame abutment portion 15 of the element abutment section 16 go closer to the curved portion 13 of the frame main body section 12. Then, the detection element 4 is pushed against the element abutment section 16 further thereby resiliently deforming the element abutment section 16 against the frame main body section 12 and abuttingly engaging the frame abutment portion 15 of the element abutment section 16 with the curved portion 13 of the frame main body section 12. By this, the element abutment section 16 is put into a state of being supported at two places, i.e., at the connection side end portion 14 and the frame abutment portion 15, i.e., put into a two-point support condition.

At the next third step, a work for inserting the detection element 4 further into the rear end side of the insertion hole 84 and changing the relative positions of the detection element 4 and the separator 82 is performed. By this, the front end side portion of the frame main body section 12 and the element abutment section 16 of the lead frame 10 are put into the condition of being placed between the detection element 4 and the inner wall surface of the insertion hole 84 (refer to FIG. 1). In this instance, the element abutment section 16 is resiliently deformed so as to allow the axially central portion thereof to extend along the plate surface of the detection element 4 and therefore put into a condition of being abuttingly engaged at a wide area with the electrode terminal section of the detection element 4.

By performing the assembly work in the above-described manner, the detection element 4, the lead frame 10 and the separator 82 can be assembled into a unit. While the resilient deformation states of the first lead frame 11 at the time of assembly work have been herein described, the second lead frame 211 exhibits the similar deformation states to the first lead frame 11.

In the meantime, at the time of insertion of the detection element 4 into the insertion hole 84, an external force is applied to the lead frame 10 in the direction to cause the frame main body section 12 apart from the inner wall surface of the insertion hole 84 due to the frictional force caused between the detection element 4 and the lead frame 10 (specifically, the element abutment section 16).

In contrast to this, the first lead frame 11 of the lead frames 10 is disposed in the insertion hole 84 in a way as to cause the first locking surface 135 and the second locking surface 137 of the first frame locking section 19 to engage the inner wall surface of the first locking groove 90. Further, the second lead frame 211 of the lead frames 10 is disposed in the insertion hole 84 so as to be put in a state where the third locking surface 235 and the fourth locking surface 237 of the second locking section 219 are engaged with the inner wall surface of the second locking groove 91.

By engagement of the first locking surface 135 of the first frame locking section 19 with the inner wall surface of the first locking groove 90, it becomes possible to inhibit the frame main body section 12 from moving axially toward the rear end side. Further, by engagement of the second locking surface 137 of the first frame locking section 19 with the inner wall surface of the first locking groove 90, it becomes possible to inhibit the frame main body section 12 from moving in the direction apart from the inner surface of the insertion hole 84. Similarly, by engagement of the third locking surface 235 of the second frame locking section 219 with the inner wall surface of the second locking groove 91, it becomes possible to inhibit the second frame main body section 212 from moving axially toward the rear end side. Further, by engagement of the fourth locking surface 237 of the second frame locking section 219 with the inner wall surface of the second locking groove 91, it becomes possible to inhibit the second frame main body section 212 from moving in the direction apart from the inner surface of the insertion hole 84.

Namely, movement of the frame main body section 12 (the second frame locking section 219) can be inhibited even in case an external force is applied to the lead frame 10, thus making it possible to prevent the relative positions of the lead frame 10 (first lead frame 11, second lead frame 211) and the detection element 4 from being varied.

Figure 7:
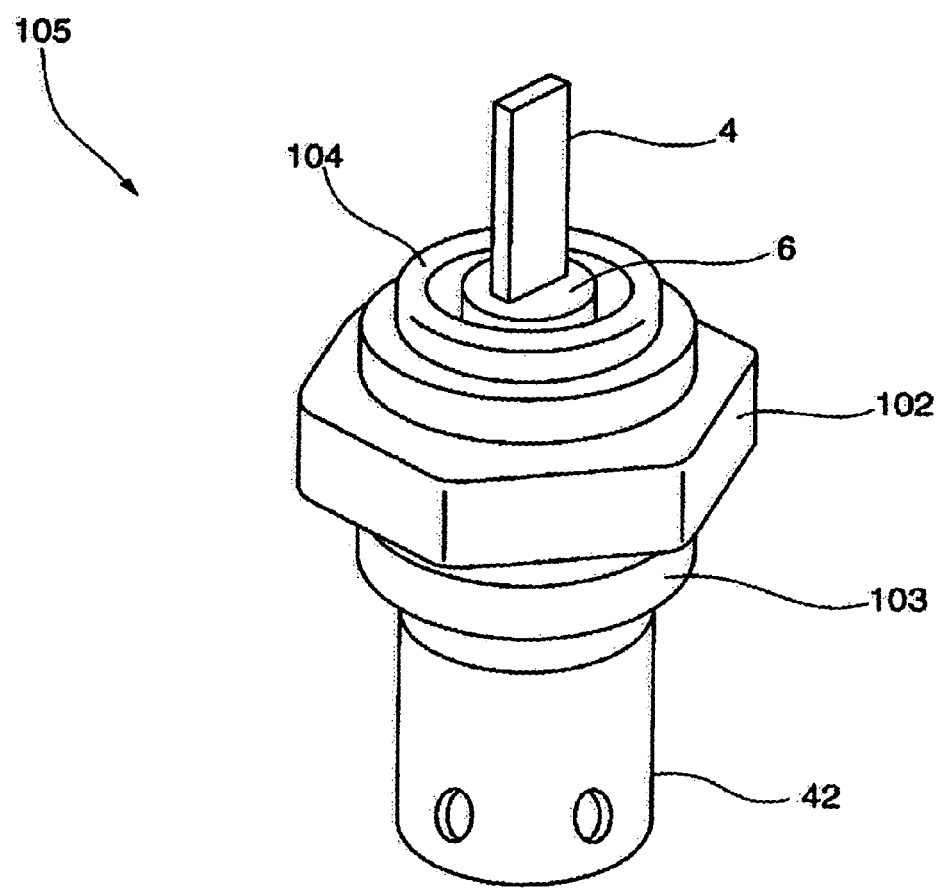
FIG. 7 is a perspective view of intermediate assembly in a state where a rear end side of the detection is protruded from a rear end portion of a metallic member and a rear end portion of a ceramic sleeve.

In the meantime, the assembly work for assembling the detection element 4, the lead frame 10 and the separator 82 into an integral unit is executed in the middle of a production process of the air/fuel ratio sensor 2. In the production process of the air/fuel ratio sensor 2, it is executed in the stage prior to the assembly work, a work for assembling an intermediate assembly part consisting of the detection element 4, the ceramic sleeve 6, the talcum ring 108, the ceramic holder 106, the metallic housing 102, etc. FIG. 7 is a perspective view of the intermediate assembly part 105 in a state where the rear end side of the detection element 4 protrudes from the rear end portion 104 of the metallic housing 102 and the rear end portion of the ceramic sleeve 6.

In the production process of the air/fuel ratio sensor 2, the lead frame 10 and the separator 82 can be attached to the detection element 4 by performing the above-described assembly work on the detection element 4 in the state of constituting the intermediate assembly part 105.

By executing, after the separator 82 and the detection element are assembled together, a fixing work, etc. for joining the outer tube 4, etc. to the metallic housing 102 by laser welding or the like and fixing the grommet 50 to the outer tube 44 by caulking, the air/fuel ratio sensor 2 is completed and the production process of the air/fuel ratio sensor 2 is finished.

In the meantime, in this embodiment, the lead frame 10 corresponds to the metallic terminal member described in "what is claimed is" and the insertion hole 84 corresponds to the element insertion hole. Of the second lead frame 211, the third locking surface 235 of the second frame locking section 219 corresponds to the first locking surface described in "what is claimed is", and the fourth locking surface 237 corresponds to the second locking surface described in "what is claimed is".

Further, of the sensor production process, the working step for disposing the lead frame 10 within the insertion hole 84 of the separator 82, disposing the first frame locking section 19 in the first locking groove 90 and disposing the second frame locking section 219 in the second locking groove 91 corresponds to the first step described in "what is claimed is", and the first step in the assembly work for assembling the detection element 4, the lead frame 10 and the separator 82 together corresponds to the second step described in "what is claimed is". Further, the second step and the third step in the assembly work for assembling the detection element 4, the lead frame 10 and the insulation contact member 82 together corresponds to the third step described in "what is claimed is".

As having been described above, the air/fuel ratio sensor 2 of this embodiment is configured to include the lead frame 10 having the frame main body section 12 and the element abutment section 16, and the lead frame 10 is configured so as to constitute part of a current path by abuttingly engaging the element abutment sections 16 with the electrode terminal sections 20, 31, 32, 34, 36 of the detection element by the effect of a restoring force caused by resilient deformation of the element abutment section 16 toward the frame main body section 12.

Of the lead frames 10, the first lead frame 11 includes the first frame locking section 19 having the first locking surface 135 and the second locking surface 137 and is configured so that the first frame locking section 19 is disposed in the first locking groove 90 of the separator 82 and the first locking surface 135 and the second locking surface 137 engage the inner wall surface of the first locking groove 90. Further, of the lead frames 10, the second lead frame 211 includes the second frame locking section 219 having the third locking surface 235 and the fourth locking surface 237 and is configured so that the second frame locking section 219 is disposed in the second locking groove 91 of the separator 82 and the third locking surface 235 and the fourth locking surface 237 engage the inner wall surface of the second locking groove 91.

In the first lead frame 11, movement of the frame main body section 12 axially toward the rear end side can be inhibited by engagement of the first locking surface 135 of the first frame locking section 19 with the inner wall surface of the first locking groove 90, and movement of the frame main body section 12 in the direction apart from the inner surface of the insertion hole 84 of the frame main body section 12 can be inhibited by engagement of the second locking surface 137 of the first frame locking section 19 with the inner wall surface of the first locking groove 90. Further, in the second lead frame 211, movement of the second frame main body section 212 axially toward the rear end side can be inhibited by engagement of the third locking surface 235 of the second frame locking section 219 with the inner wall surface of the second locking groove 91, and movement of the second main body section 212 in the direction apart from the inner surface of the insertion hole 84 can be inhibited by engagement of the fourth locking surface 237 of the second frame locking section 219 with the inner wall surface of the second locking groove 91.

Namely, movement of the frame main body section 12 (second frame main body section 212) can be inhibited even in the case an external force is applied to the lead frame 10, thus making it possible to prevent the relative positions of the lead frame 10 and the detection element 4 from being varied.

Accordingly, by this embodiment, a variation in the relative positions of the lead frame 10 and the detection element 4 can be prevented even in the case an inadequate external force is applied to the lead frame 10, and the electrical connection of the lead frame 10 with the electrode terminal sections 30, 31, 32, 34, 36 can be maintained suitably.

As a result, at the time of the assembly work of assembling the detection element 4, the lead frame 10 and the separator 82 together, buckling of the lead frame 10 is hard to be caused, therefore the frequency at which a defective is caused in the sensor production work can be decreased, and the sensor production efficiency can be improved.

Further, the air/fuel ratio sensor 2 of this embodiment is constructed to use the lead frame 10 (first lead frame 11, second lead frame 211) which is configured so that the support condition of the element abutment section 16 which is brought into contact with the electrode terminal section of the detection element 4 varies from the one-point support condition to the two-point support condition.

The lead frame 10 in a state where the frame abutment portion 15 (second frame abutment portion 215) of the element abutment section 16 is not engaged with the frame main body section 12 (second frame main body section 212), i.e., in the one-point support condition is configured so as to push the element abutment section 16 against the electrode terminal section of the detection element 4 with a small stress caused by resilient deformation of the connection side end portion 14 (second connection side end portion 214) and its adjacent portion. Further, in case the frame abutment portion 15 (second frame abutment portion 215) is abuttingly engaged with the frame main body section 12 (second frame main body section 212), the lead frame 10 produces a large stress due to resilient deformation of the axially central portion of the element abutment section 16 (second element abutment section 216).

Namely, the lead frame 10 is configured to produce a larger pressure for pressing the element abutment section 16 (second element abutment section 216) against the detection element 4 when in the two-point support condition where the frame abutment portion 15 (second frame abutment portion 215) of the element abutment section 16 (second element abutment section 216) is abuttingly engaged with the frame main body section 12 (second frame main body section 212) than when in the one-point support condition where the frame abutment portion 15 (second frame abutment portion 215) of the element abutment section 16 (second element abutment section 216) is not abuttingly engaged with the frame main body section 12 (second frame main body section 212).

By this, at the time of assembling the lead frames 10 and the detection element 4 together in the production process of the air/fuel ratio sensor 2, the element abutment sections 16 (second element abutment sections 216) of the lead frames 10 are pressed against the electrode terminal sections 30, 31, 32, 34, 36 with a relatively smaller force in the first half stage of the assembly work. As a result, at the time of the assembly work for assembling the lead frames 10 and the detection element 4, it becomes possible to prevent an excessively large pressure from being caused by resilient deformation of the lead frame 10 and applied to the detection element 4, and it becomes possible to inhibit the detection element 4 from being broken by application of pressure.

Further, after the assembly work is completed, the element abutment section 16 (second element abutment section 216) is brought into the two-point support condition of being supported at the connection side end portion 14 (second connection side end portion 214) and the frame abutment portion 15 (second frame abutment portion 215) upon the frame main body section 12 (second frame main body section 212). By a large stress (resilient force) caused by resilient deformation of the element abutment section 16 (second element abutment section 216) in the two-point support condition, the element abutment section 16 (second element abutment section 216) itself of the lead frame 10 is pressed against the electrode terminal section of the detection element 4, thus making good the condition of electrical connection between the lead frame 10 and the detection element 4.

For this reason, it is unnecessary to make the lead frame 10 larger in the width and thickness for the purpose of attaining a large resilient force and thereby making good the condition of connection between the lead frame 10 and the detection element 4. Namely, as compared with a lead frame having an element abutment section in a one-point support condition, the lead frame 10 of this embodiment has an advantage of being able to be smaller in the width and thickness for producing an equal resilient force.

While the embodiment of this invention has been described as above, the invention is not limited to the above-described embodiment (hereinafter also referred to as the first embodiment) but can be of various other embodiments.

Then, a second wide-range air/fuel ratio sensor (hereinafter also referred to as a second air/fuel ratio sensor) with a lead frame having a wide protrusion portion that protrudes in the width direction according to the second embodiment will be described.

In the meantime, since the second air/fuel ratio sensor is different from the air/fuel ratio sensor 2 of the first embodiment in that a lead frame and separator are formed into different shapes but other members (metallic housing member, detection element, etc.) are similar in shape, description will hereinafter be made mainly to the lead frame and the separator.

The second air/fuel ratio sensor includes a third lead frame 251, a fourth lead frame 253 and a second separator 182.

First, the second separator 182 will be described.

Figure 8:
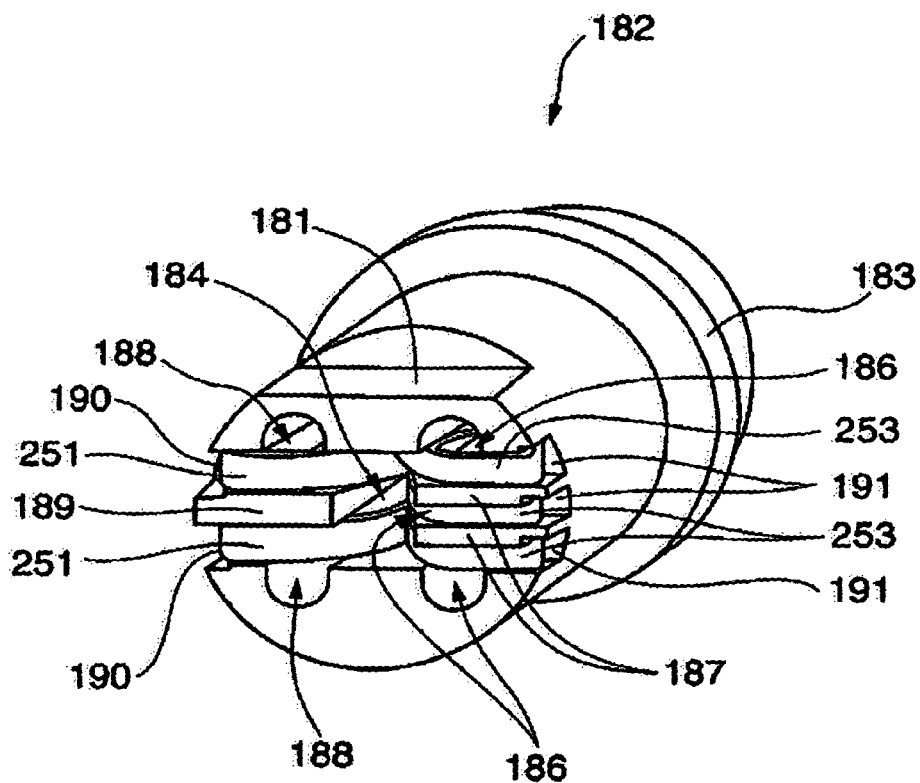
FIG. 8 is a perspective view showing an external appearance of a second separator.

In FIG. 8 is shown a perspective view of an external appearance of the second separator 182 when observed from the front end side thereof. In the meantime, in FIG. 8, the second separator 182 in the state where the third lead frame 251 and the fourth lead frame 253 are disposed in a second insertion hole 184 is shown in a perspective view.

As shown in FIG. 8, the second separator 182 is formed into a tubular shape having the second insertion hole 184 extending axially therethrough and has a second flange portion 183 protruding axially outward from an external surface thereof. The second separator 182 is abuttingly engaged at the second flange portion 183 with the outer tube side support portion 64 of the outer tube 44 and thereby disposed inside the outer tube 44. In the meantime, the outer tube side support portion 64 is formed so as to protrude inward of the outer tube 44.

At the inner wall surface of the second insertion hole 184, which faces the first plate surface 21 of the detection element 4 (refer to FIG. 1) are formed two first rib portions 187 that protrude inward. The first rib portions 187 are provided to serve as lead frame boundary portions inside the insertion hole for forming boundaries of three narrow frame disposition grooves 186 for disposing three fourth lead frames 253 separately and in a state of being electrically insulated from each other. The three narrow frame disposition grooves 186 are formed at the positions corresponding to the electrode terminal sections 30, 31 and 32 at the first plate surface 21 of the detection element 4.

Further, at the inner wall surface of the second insertion hole 184, which faces the second plate surface 23 of the detection element 4 (refer to FIG. 1), is formed one second rib portion 189 that protrudes inward. The second rib portion 189 is provided to serve as a lead frame boundary portion inside the insertion hole for forming a boundary of two wide frame disposition holes 188 for disposing two third lead frames 251 separately and in a state of being electrically insulated from each other. The two wide frame disposition grooves 188 are formed at the positions corresponding to the electrode terminal sections 34, 36 at the second plate surface 23 of the detection element 4.

The first rib portion 187 and the second rib portion 189 have a function of preventing the lead frames disposed in the adjacent frame disposition grooves from contacting each other and can prevent the adjacent lead frames from being electrically connected to each other and thereby prevent the electrical path from being deteriorated.

Further, the second separator 182 has at the front end surface (this side surface in the figure) wide locking grooves 190 and narrow locking grooves 191 that are joined to the front end side opening portion of the second insertion hole 184.

The wide locking groove 190 is formed so as to have a nearly L-shaped section with respect to a plane perpendicular to the axial direction and so as to dispose therein a first wide connection portion 271 and a second wide connection portion 273 of the third lead frame 251, which will be described later. In the meantime, the wide locking grooves 190 are formed at two portions joined to the two wide locking grooves 190.

The narrow locking groove 191 is formed so as to have a nearly L-shaped section with respect to a plane perpendicular to the axial direction and so as to dispose therein a first narrow connection portion 321 and a second narrow connection portion 323 of the fourth lead frame 253, which will be described later. In the meantime, the narrow locking grooves 191 are formed at three portions joined to the three narrow frame disposition grooves 186.

Then, the third lead frame 251 and the fourth lead frame 253 will be described.

Figure 9A:
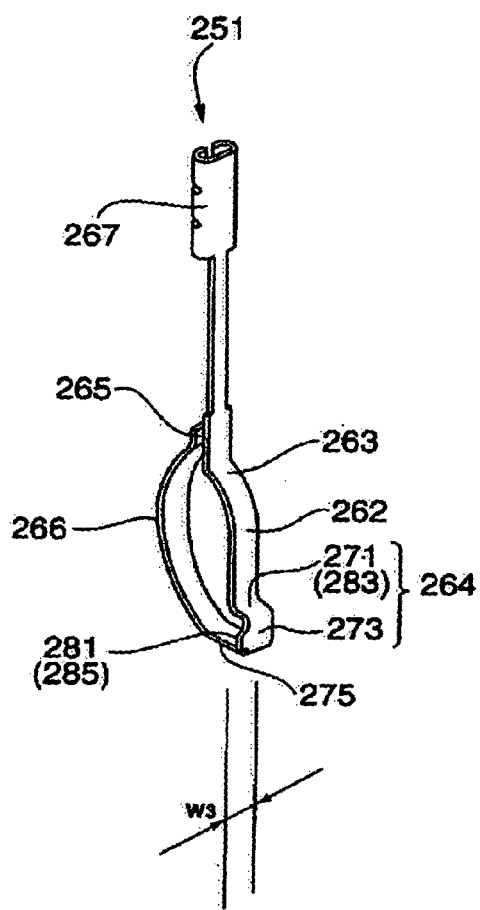
FIG. 9 is a perspective view including FIG. 9A and FIG. 9B showing external appearances of a third lead frame 251 and fourth lead frame 253, respectively.
Figure 9B:
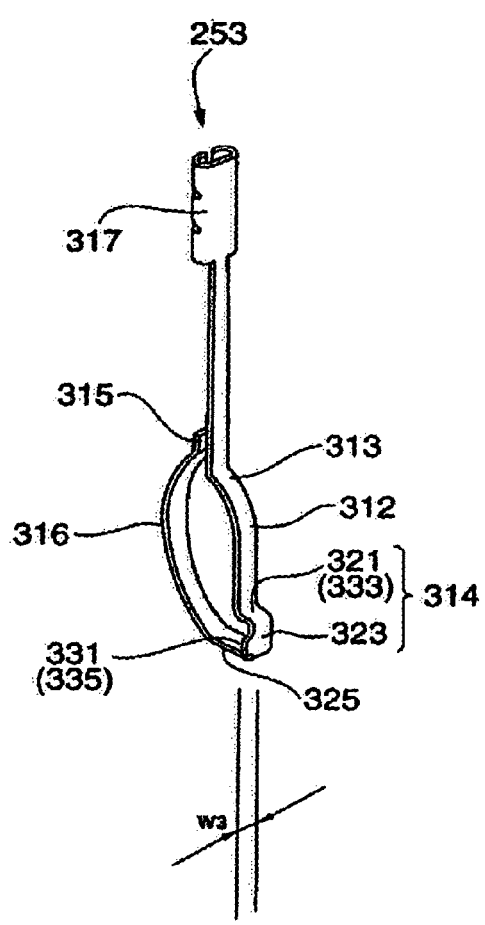

FIG. 9 is a perspective view showing external appearances of the third lead frame 251 and the fourth lead frame 253.

The third lead frame 251 includes a third frame main body section 262 formed from a long, axially extending plate and a third element abutment section 266 extending so that at least a portion thereof is disposed between the third frame main body section 262 and the detection element 4, and is configured so that the third element abutment section 266 (specifically, a portion of the third element abutment section 266) is abuttingly engaged with an electrode terminal section of the detection element 4.

The third frame main body section 262 includes a third curved portion 263 at a nearly axially central position and is configured so that a front end side portion positioned closer to the front end than the third curved portion 263 and a rear end side portion positioned closer to the rear end than the third curved portion 263 are different in the position with respect to the plate surface thickness direction. Further, the third frame main body section 262 is formed so as to be 1.2 mm in the plate surface width size W3 and 0.2 mm in the thickness.

Herein, the term "width size" is herein used to indicate the size in the direction perpendicular both to the axial direction and to the direction in which the third element abutment section 266 and the third frame main body section 262 are spaced from each other. Further, the third lead frame 251 is smaller in the width size and in the thickness as compared with the conventional lead frame.

A wide connection section 264 constituting part of the third frame main body section 262 of the third lead frame 251 is configured to include a first wide connection portion 271 and a second wide connection portion 273 and further include a wide protrusion portion 281 that protrudes from one side surface of the second wide connection portion 273 in the width direction of the second wide connection portion 273. In the meantime, the front end of the second wide connection portion 273 is connected to a third connection side end portion 275 of the third element abutment section 266.

The first wide connection portion 271 extends from a front end side portion of the third frame main body section 262 in the direction of an intervening space between the third frame main body section 262 and the third element abutment section 266 and in the direction apart from the third element abutment section 266.

The second wide connection portion 273 extends from the end of the first wide connection portion 271 on the side remoter from the third element abutment section 266, axially toward the front end of the third frame main body section 262.

The first wide connection portion 271 of the third lead frame 251 has a first locking surface 283 that faces axially toward the rear end side of the third lead frame 251. Further, the wide protrusion portion 281 of the third lead frame 251 has a second locking surface 285 facing in the direction of an intervening space between the third frame main body section 262 and the third element abutment section 266 and toward the third element abutment section 266 (detection element 4).

Namely, the wide connection section 264 is configured to have the first locking surface 283 and the second locking surface 285 and corresponds to the frame locking section described in "what is claimed is".

The third element abutment section 266 is configured so that when the third lead frame 251 itself is in a free state, a third frame abutment portion 265 that is an axial rear end portion of the third element abutment section 266 is put in a state of being spaced apart from the third frame main body section 262. Further, the third element abutment section 266 is formed into a circular arc shape which is so curved as to allow the space between the axially central portion thereof and the third frame main body section 262 to be larger as compared with the space between the third frame abutment portion 265 and the third frame main body section 262 and to allow the convex side surface of the circular arc shape to an electrode terminal section of the detection element 4.

In the meantime, the third element abutment section 266 is configured to resiliently deform at the third connection side end portion 27 and a portion adjacent thereto and continue resilient deformation toward the third frame main body section 262 thereby allowing the third frame abutment portion 265 to abuttingly engage the third frame main body section 262.

Further, the third lead frame 251 is configured so that when there is no external force applied thereto and the third element abutment section 266 is not resiliently deformed (when in a free state), the space between the third frame abutment portion 265 of the third element abutment section 266 and the third main body section 262 is smaller than the depth size of the wide frame disposition groove 188 of the second separator 182.

In the meantime, the third lead frame 251 is configured so that when the third element abutment section 266 is placed between the detection element 4 and the second separator 182 and resiliently deformed toward the third frame main body section 262, the third frame abutment portion 265 of the third element abutment section 266 is abuttingly engaged with the third frame main body section 262 and at least a portion of the third element abutment section 266 is disposed outside the wide frame disposition groove 188 to abuttingly engage an electrode terminal section of the detection element 4.

Further, the third lead frame 251 has a third lead wire connection section 267 connected to a rear end (upper end portion in the figure) of the third frame main body section 262. The third lead wire connection section 267 is formed into a nearly tubular shape by bending and then caulked radially inward under a condition of having a core line of the lead wire 46 (not shown) inserted thereinto thereby being electrically connected to the lead wire 46. In the meantime, FIG. 9 shows the third lead wire connection section 267 in a state of being formed into a nearly tubular shape.

Then, the fourth lead frame 253 includes a fourth frame main body section 312 formed from a long, axially extending plate and a fourth element abutment section 316 extending so that at least a portion thereof is disposed between the fourth frame main body section 312 and the detection element 4, and is configured so that the fourth element abutment section 316 (specifically, a portion of the fourth element abutment section 316) abuttingly engages an electrode terminal section of the detection element 4.

The fourth frame main body section 312 includes a fourth curved portion 313 at an axially nearly central position and is configured so that a front end side portion positioned closer to the front end than the fourth curved portion 313 and a rear end side portion positioned closer to the rear end than the fourth curved portion 313 are different in the position with respect to the plate surface thickness direction. Further, the fourth frame main body section 312 is formed so as to be 0.8 mm in the plate surface width size W4 and 0.2 mm in the thickness.

Herein, the term "width size" is herein used to indicate the size in the direction perpendicular both to the axial direction and to the direction of an intervening space between the fourth element abutment section 316 and the fourth frame main body section 312. Further, the fourth lead frame 253 is smaller in the width size and in the thickness as compared with the conventional lead frame.

A narrow connection section 314 of the fourth lead frame 253 is configured to include a first narrow connection portion 321 and a second narrow connection portion 323 and further include a wide protrusion portion 331 that protrudes from the side surface of the second narrow connection portion 323 in the width direction of the second narrow connection portion 323. In the meantime, the front end of the second narrow connection portion 323 is connected to a fourth connection side end portion 325 of the fourth element abutment section 316.

The first narrow connection portion 321 extends from the front end side portion of the fourth frame main body section 312 in the direction of an intervening space between the fourth frame main body section 312 and the fourth element abutment section 316 and in the direction apart from the fourth element abutment section 316.

The second narrow connection portion 323 extends from the end of the first narrow connection portion 321, which is on the side remoter from the fourth element abutment section 316, axially toward the front end of the fourth frame main body section 312.

The first narrow connection portion 321 of the fourth lead frame 253 has a first locking surface 333 that faces axially toward the rear end side of the fourth lead frame main body section 312. Further, the second wide protrusion portion 331 of the fourth lead frame 253 has a second locking surface 335 that faces in the direction of an intervening space between the fourth frame main body section 312 and the fourth element abutment section 316 and toward the fourth element abutment section 316 (detection element 4 side).

Namely, the narrow connection section 314 is configured to have the first locking surface 333 and the second locking surface 335 and corresponds to the frame locking section described in "what is claimed is".

The fourth element abutment section 316 is configured so that when the fourth lead frame 253 itself is in a free state, the fourth frame abutment portion 315 that is an axially rear end portion of the fourth element abutment section 316 is in a state of being spaced apart from the fourth frame main body section 312. Further, the fourth element abutment section 316 is formed into a circular arc shape which is so curved as to allow the space between the axially central portion thereof and the fourth frame main body section 312 to be larger as compared with the space between the fourth frame abutment portion 315 and the fourth frame main body section 231 and to allow the convex side surface of the circular arc shape to abuttingly engage an electrode terminal section of the detection element 4.

In the meantime, the fourth element abutment section 316 is configured to resiliently deform at the third connection side end portion and a portion adjacent thereto and continue resilient deformation toward the fourth frame main body section 312 for thereby allowing the fourth frame abutment portion 315 to abuttingly engage the fourth frame main body section 312.

Further, the fourth lead frame 253 is configured so that when there is no external force applied to the fourth lead frame and the fourth element abutment section 316 is not resiliently deformed (when in a free condition), the space between the fourth frame abutment portion 315 of the fourth element abutment section 316 and the fourth frame main body section 312 is smaller than the depth size of the narrow frame disposition groove 186 of the second separator 182.

In the meantime, the fourth lead frame 253 is configured so that when placed between the detection element 4 and the second separator 182 to allow the fourth element abutment section 316 to resiliently deform toward the fourth frame main body section 312, the fourth frame abutment portion 315 of the fourth element abutment section 316 is abuttingly engaged with the fourth frame main body section 312 and at least a portion of the fourth element abutment section 316 is disposed outside the narrow frame disposition groove 186 to abuttingly engage an electrode terminal section of the detection element 4.

Further, the fourth lead frame 253 has a fourth lead wire connection section 317 connected to a rear end (upper end portion in the figure) of the fourth frame main body section 312. The fourth lead wire connection section 317 is formed into a nearly tubular shape by bending and then caulked radially inward under a condition of having a core line of the lead wire 46 inserted thereinto thereby being electrically connected to the lead wire 46 (not shown). In the meantime, FIG. 9 shows the fourth lead wire connection section 317 in a state of being formed into a nearly tubular shape.

As shown in FIG. 8, in case the third lead frame 251 is disposed in the second insertion hole 184, the first wide connection portion 271 and the wide protrusion portion 281 of the third lead frame 251 are disposed in the wide locking groove 190 of the second separator 182. As a result, the first locking surface 283 of the first wide connection portion 271 and the second locking surface 285 of the wide protrusion portion 281 are put into a condition of being engaged with the inner wall surface of the wide locking groove 190.

Further, in case the fourth lead frame 251 is disposed in the second insertion hole 184, the first narrow connection portion 321 and the second wide protrusion portion 331 of the fourth lead frame 253 are disposed in the narrow locking groove 191 of the second separator 182. As a result, the first locking surface 333 of the first narrow connection portion 321 and the second locking surface 335 of the second wide protrusion portion 331 are put into a condition of being engaged with the inner wall surface of the narrow locking groove 191.

In the meantime, the third lead frame 251 is disposed in the second insertion hole 184 through insertion into the second insertion hole 184 of the second separator 182 together with the lead wire 46 after the lead wire 46 is connected to the third lead wire connection section 267 (second lead wire connection section 217). Further, the fourth lead frame 253 is disposed in the second insertion hole 184 through insertion into the second insertion hole 184 of the second separator 182 together with the lead wire 46 after the fourth lead wire connection section 317 is connected with the lead wire 46.

By inserting the detection element 4 into the contact insertion hole 184 of the second separator 182 in a state of disposing therein the third lead frames 251 and the fourth lead frames 253 in the above-described manner, the third element abutment sections 266 of the third lead frames 251 can be electrically connected to the electrode terminal sections 34, 36 of the detection element 4 and the fourth element abutment sections 316 of the fourth lead frames 253 can be electrically connected to the electrode terminal sections 30, 31, 32.

In the meantime, in the second embodiment, the third lead frame 251 and the fourth lead frame 253 correspond to the metallic terminal members described in "what is claimed is", and the second insertion hole 184 corresponds to the insertion hole. Further, of the third lead frame 251, the first locking surface 283 of the first wide connection portion 271 corresponds to the first locking surface described in "what is claimed is" and the second locking surface 285 of the wide protrusion portion 281 corresponds to the second locking surface described in "what is claimed is". Further, of the fourth lead frame 253, the first locking surface 333 of the first narrow connection portion 321 corresponds to the first locking surface described in "what is claimed is" and the second locking surface 335 of the second wide protrusion portion 331 corresponds to the second locking surface described in "what is claimed is".

Further, the first wide connection portion 271 and the first narrow connection portion 321 correspond to the first connection portions described in "what is claimed is", the second wide connection portion 273 and the second narrow connection portion 323 correspond to the second connection portions, and the wide protrusion portion 281 and the second wide protrusion portion 331 correspond to the wide protrusion portion.

As having been described above, the second air/fuel ratio sensor according to the second embodiment has the third lead frame 251 with the first locking surface 283 and the second locking surface 285 and is configures so that the first locking surface 283 and the second locking surface 285 are abuttingly engaged with the inner wall surface of the wide locking groove 190.

By such engagement of the first locking surface 283 of the third lead frame 251 with the inner wall surface of the wide locking groove 190, it becomes possible to inhibit the third frame main body section 262 from moving axially toward the rear end side. Further, by engagement of the second locking surface 285 with the inner wall surface of the wide locking groove 190, it becomes possible to inhibit the third frame main body section 262 from moving in the direction apart from the inner surface of the second insertion hole 184.

Further, the fourth lead frame 253 has the first locking surface 333 and the second locking surface 335, and the first locking surface 333 and the second locking surface 335 are abuttingly engaged with the inner wall surface of the narrow locking groove 191.

By such engagement of the first locking surface 333 of the fourth lead frame 253 with the inner wall surface of the narrow locking groove 191, it becomes possible to inhibit the fourth frame main body section 312 from moving axially toward the rear end side. Further, by engagement of the second locking surface 335 with the inner wall surface of the narrow locking groove 191, it becomes possible to inhibit the fourth frame main body section 312 from moving in the direction apart from the inner surface of the second insertion hole 184.

Namely, movement of the third frame main body section 262 and the fourth frame main body section 312 can be inhibited even in case an external force is applied to the third lead frame 251 and the fourth lead frame 253, thus making it possible to prevent the relative positions of the third lead frame 251 and the detection element 4 and the relative positions of the fourth lead frame 253 and the detection element 4 from being varied.

Accordingly, by the second embodiment, a variation in the relative positions of the lead frame and the detection element 4 can be prevented even in case an inadequate external force is applied to the lead frames at the time of use of the third lead frame 251 and the fourth lead frame 253 which are formed small in the width size and in the thickness, and the electrical connection of the lead frames with the electrode terminal sections 30, 31, 32, 34, 36 can be maintained suitably.

As a result, at the time of the assembly work of assembling the detection element 4, the lead frames and the separator 182 together, buckling of the lead frames is hard to be caused, therefore the frequency at which a defective is caused in the sensor production work can be decreased, and the sensor production efficiency can be improved.

Further, the fourth lead frame 253 does not have the second wide protrusion portion 331 at each side of the second narrow connection portion 323 but at one side surface of the second narrow connection portion 323. This makes it possible to prevent a part of the first rib portion 187 of the second separator, in which the second wide protrusion portion 331 is disposed, from becoming too thin, thus enabling the second separator 182 to have such structure that is hard to break.

In brief, in case the second protrusion portions 331 are provided to the both side surfaces of the second narrow connection portion 323, the first rib portion 187 needs to be formed thin in order to obtain the disposition areas (narrow locking grooves 191) for disposition of the respective second wide protrusions 331 of the two adjacently disposed fourth lead frames 253.

In contrast to this, by using the fourth lead frame 253 in which the second wide protrusion 331 is provided to only one side surface of the narrow connection portion 323, it becomes possible to prevent the first rib portion 187 from becoming too thin at a portion thereof and obtain a sensor with the second separator 182 being hard to break.

Then, a third wide-range air/fuel ratio sensor (hereinafter also referred to as a second air/fuel ratio sensor) with a lead frame having a wide protrusion portion that protrudes in the width direction according to the third embodiment will be described.

In the meantime, since the third air/fuel ratio sensor is different from the air/fuel ratio sensor 2 of the first embodiment in that a lead frame and separator are formed into different shapes but other members (metallic housing member, detection element, etc.) are similar in shape, description will hereinafter be made mainly to the lead frame and the separator.

The third air/fuel ratio sensor includes a fifth lead frame 351, a sixth lead frame 353 and a third separator 282.

First, the third separator 282 will be described.

Figure 10:
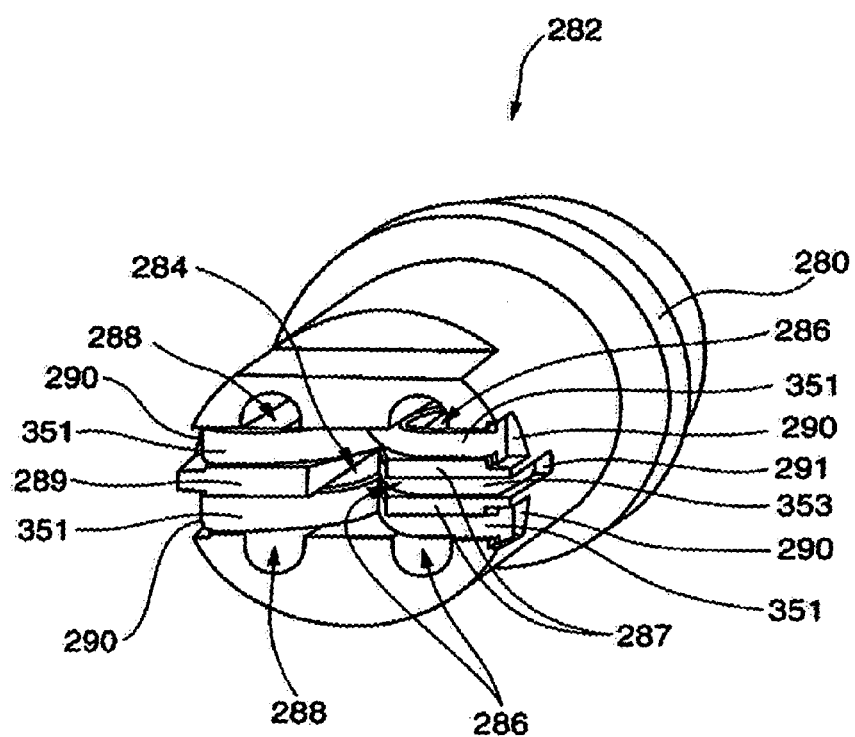
FIG. 10 is a perspective view showing an external appearance of a third separator.

In FIG. 10 is shown a perspective view of an external appearance of the third separator 282 when observed from the front end side thereof. In the meantime, in FIG. 10, the third separator 282 in the state where the fifth lead frame 351 and the sixth lead frame 353 are disposed in a third insertion hole 284 is shown in a perspective view.

As shown in FIG. 10, the third separator 282 is formed into a tubular shape having the third insertion hole 284 extending axially therethrough and has a third flange portion 280 protruding axially outward from an external surface thereof. The third separator 282 is abuttingly engaged at the third flange portion 280 with the outer tube side support portion 64 of the outer tube 44 and thereby disposed inside the outer tube 44. In the meantime, the outer tube side support portion 64 is formed so as to protrude inward of the outer tube 44 (refer to FIG. 1).

At the inner wall surface of the third insertion hole 284, which faces the first plate surface 21 (not shown) of the detection element 4 are formed two first rib portions 287 that protrude inward. The first rib portions 287 are provided to serve as lead frame boundary portions inside the insertion hole for forming boundaries of three narrow frame disposition grooves 286 for disposing two fifth lead frames 353 and one sixth lead frame 353 separately and in a state of being electrically insulated from each other. The three narrow frame disposition grooves 286 are formed at the positions corresponding to the electrode terminal sections 30, 31 and 32 at the first plate surface 21 of the detection element 4.

Further, at the inner wall surface of the third insertion hole 284, which faces the second plate surface 23 of the detection element 4 (not shown), is formed one second rib portion 289 that protrudes inward. The second rib portion 289 is provided to serve as a lead frame boundary portion inside the insertion hole for forming a boundary of two wide frame disposition grooves 288 for disposing two fifth lead frames 351 separately and in a state of being electrically insulated from each other. The two wide frame disposition grooves 288 are formed at the positions corresponding to the electrode terminal sections 34, 36 at the second plate surface 23 of the detection element 4.

The first rib portion 287 and the second rib portion 289 have a function of preventing the lead frames disposed in the adjacent frame disposition grooves from contacting each other and can prevent the adjacent lead frames from being electrically connected to each other and thereby prevent the electrical path from being deteriorated.

Further, the third separator 282 has at the front end surface (this side surface in the figure) third wide locking grooves 290 and third narrow locking grooves 291 that are joined to the front end side opening portion of the third insertion hole 284.

The third wide locking groove 290 is formed so as to have a nearly T-shaped section with respect to a plane perpendicular to the axial direction and be capable of disposing therein a first wide connection portion 271 and a second wide connection portion 273 of the fifth lead frame 351, which will be described later.

The third narrow locking groove 291 has a radial groove portion that is formed to extend from the front end side opening portion of the third insertion hole 284 radially outward of the third separator 282. Further, the third narrow locking 291 is formed so as to be capable of disposing therein a first narrow frame connection portion 421 and a second narrow frame connection portion 423 of the sixth lead frame 353, which will be described later. In the meantime, the third narrow locking groove 291 is formed at a portion connected to central one of the three narrow frame disposition grooves 286 that are arranged side by side.

Then, the fifth lead frame 351 and the sixth lead frame 353 will be described. FIG. 11 is a perspective view showing external appearances of the fifth lead frame 351 and the sixth lead frame 353.

The fifth lead frame 351 is constituted by adding a wide protrusion to the third lead frame 251. Namely, the fifth lead frame 351 is configured to include a wide protrusion portion 281 protruding from one side surface of the second wide connection portion 273 in the width direction of the second wide connection portion 273 and a third wide protrusion portion 381 protruding from the other side surface of the second wide connection portion 273 in the width direction of the second wide connection portion 273.

In the figure, the portions common to the fifth lead frame 351 and the third lead frame 251 are designated by the same reference characters as the third lead frame 251.

The fifth lead frame 351 is configured to include a fourth wide connection section 364, and the fourth wide connection section 364 is configured to include a first wide connection portion 271, a second wide connection portion 273, the wide protrusion portion 281 and the third wide protrusion portion 381. In the meantime, the front end of the second wide connection portion 273 is connected to the third connection side end portion 275 of the third element abutment section 266.

Further, the third wide protrusion portion 381 of the fifth lead frame 351 has a fifth locking surface 385 that faces in the direction of an intervening space between the third frame main body section 262 and the third element abutment section 266 and toward the third element abutment section 266 side.

Namely, the fourth wide connection section 364 is configured to include a first locking surface 283, a second locking surface 285 and the fifth locking surface 385 and corresponds to the frame locking section described in "what is claimed is".

Then, the sixth lead frame 353 includes a sixth frame main body section 412 formed from a long, axially extending plate and a sixth element abutment section 416 extending so that at least a portion thereof is disposed between the sixth frame main body section 412 and the detection element 4, and is configured so that the sixth element abutment section 416 (specifically, a portion of the sixth element abutment section 416) is abuttingly engaged with an electrode terminal section of the detection element 4.

The sixth frame main body section 412 includes a sixth curved portion 413 at a nearly axially central position and is configured so that a front end side portion positioned closer to the front end than the sixth curved portion 413 and a rear end side portion positioned closer to the rear end than the sixth curved portion 413 are different in the position with respect to the plate surface thickness direction.

The narrow frame connection section 414 of the sixth lead frame 353 is configured to include a first narrow frame connection portion 421 and a second narrow connection portion 413 and a third narrow frame connection portion 425.

The first narrow frame connection portion 421 extends from the front end side portion of the sixth frame main body section 412 in the direction of an intervening space between the sixth frame main body section 412 and the sixth element abutment section 416 and in the direction apart from the sixth element abutment section 416.

The second narrow frame connection portion 423 extends from the end portion of the first narrow frame connection portion 421 on the side remoter from the sixth element abutment section 416, axially toward the rear end side of the sixth frame main body section 412.

The third narrow frame connection portion 425 is extended from the end portion of the second narrow frame connection portion 423 on the side opposite to the connection side for connection with the first narrow frame connection portion 421, bent axially toward the front end side of the sixth frame main body section 412 and connected at a portion closer to the front end than the first narrow frame connection portion 421.

The first narrow frame connection portion 421 has a first locking surface 433 that faces axially toward the rear end side of the sixth frame main body section 412. Further, the second narrow frame connection portion 423 has a second locking surface 435 that faces in the direction of an intervening space between the sixth frame main body section 412 and the sixth element abutment section 416 and toward the sixth element abutment section 416.

Namely, the narrow frame connection section 414 is configured to include the first locking surface 423 and the second locking surface 435 and corresponds to the frame locking section described in "what is claimed is".

The sixth element abutment section 416 is connected at the front end thereof to the front end of the sixth frame main body section 412 (the front end of the third narrow frame connection portion 425) and is configured so that when the sixth lead frame 353 itself is in a free state, the sixth frame abutment portion 415 that is an axially rear end portion of the sixth element abutment section 416 is in a state of being spaced apart from the sixth frame main body section 412. Further, the sixth element abutment section 416 is formed into a circular arc shape which is so curved as to allow the space between the axially central portion thereof and the sixth frame main body section 412 to be larger as compared with the space between the fourth frame abutment portion 315 and the sixth frame main body section 412 and to allow the convex side surface of the circular arc shape to abuttingly engage an electrode terminal section of the detection element 4.

In the meantime, the sixth element abutment section 416 is configured to resiliently deform at the front end side end portion and a portion adjacent thereto and continue resilient deformation toward the sixth frame main body section 412 for thereby allowing the sixth frame abutment portion 416 to abuttingly engage the sixth frame main body section 412.

Further, the sixth lead frame 353 is configured so that when there is no external force applied thereto and the sixth element abutment section 416 is not resiliently deformed (when in a free state), the space between the sixth frame abutment portion 415 of the sixth element abutment section 416 and the sixth frame main body section 412 is smaller than the depth size of the frame disposition groove 286 of the third separator 282.

In the meantime, the sixth lead frame 353 is configured so that when placed between the detection element 4 and the third separator 282 to allow the sixth element abutment section 416 to resiliently deform toward the sixth frame main body section 412, the sixth frame abutment portion 415 of the sixth element abutment section 416 is abuttingly engaged with the sixth frame main body section 412 and at least a portion of the sixth element abutment section 416 is disposed outside the frame disposition groove 286 to abuttingly engage an electrode terminal section of the detection element 4.

Further, the sixth lead frame 353 has a sixth lead wire connection section 417 connected to a rear end portion (upper end portion in the figure) of the sixth frame main body section 412. The sixth lead wire connection section 417 is formed into a nearly tubular shape by bending and then caulked radially inward under a condition of having the core line of the lead wire 46 inserted thereto thereby being electrically connected to the lead wire 46 (not shown). In the meantime, FIG. 11 shows the sixth lead wire connection section 417 in a state of being formed into a nearly tubular shape.

As shown in FIG. 10, in case the fifth lead frame 351 is disposed in the third insertion hole 284, the first wide connection portion 271, the wide protrusion portion 281 and the third wide protrusion portion 381 of the fifth lead frame 351 are disposed in the third wide locking groove 290 of the third separator 282. As a result, the first locking surface 283 of the first wide connection portion 271, the second locking surface 285 of the wide protrusion portion 281 and the fifth locking surface 385 of the third wide protrusion portion 381 are put into a condition of being engaged with the inner wall surface of the third wide locking groove 290.

Further, in case the sixth lead frame 353 is disposed in the third insertion hole 284, the first narrow frame connection portion 421 and the second narrow frame connection portion 423 of the sixth lead frame 353 are disposed in the third narrow locking groove 291 of the third separator 282. As a result, the first locking surface 433 of the first narrow frame connection portion 421 and the second locking surface 435 of the second narrow frame connection portion 423 are put into a condition of being engaged with the inner wall surface of the third narrow locking groove 291.

In the meantime, the fifth lead frame 351 is disposed in the third insertion hole 284 through insertion into the third insertion hole 284 of the third separator 282 together with the lead wire 46 after the lead wire 46 is connected to the third lead wire connection section 267. Further, the sixth lead frame 353 is disposed in the third insertion hole 284 through insertion into the third insertion hole 284 of the third separator 282 together with the lead wire 46 after the sixth lead wire connection section 417 is connected with the lead wire 46.

By inserting the detection element 4 into the third insertion hole 284 of the third separator 282 in a state of disposing therein the fifth lead frames 351 and the sixth lead frame 353 in the above-described manner, the third element abutment sections 266 of the fifth lead frame 351 can be electrically connected to the electrode terminal sections 30, 32, 34, 36 of the detection element 4 and the sixth element abutment section 316 of the sixth lead frames 253 can be electrically connected to the electrode terminal section 31 of the detection element 4.

In the meantime, in the third embodiment, the fifth lead frame 351 and the sixth lead frame 353 correspond to the metallic terminal members described in "what is claimed is", and the third insertion hole 284 corresponds to the insertion hole. Further, of the fifth lead frame 351, the first locking surface 283 of the first wide connection portion 271 corresponds to the first locking surface described in "what is claimed is" and the second locking surface 285 of the wide protrusion portion 281 corresponds to the second locking surface described in "what is claimed is".

Further, of the sixth lead frame 353, the first narrow frame connection portion 421 corresponds to the first frame connection portion described in "what is claimed is", the second narrow frame connection portion 423 corresponds to the second frame connection portion and the third narrow frame connection portion 425 corresponds to the third frame connection portion. Further, of the sixth lead frame 353, the first locking surface 433 of the first narrow frame connection portion 421 corresponds to the first locking surface described in "what is claimed is" and the second locking surface 435 of the second narrow frame connection portion 423 corresponds to the second locking surface described in "what is claimed is".

As having been described above, the third air/fuel ratio sensor according to the third embodiment has the fifth lead frame 351 with the first locking surface 283, the second locking surface 285 and the fifth locking surface 385, and is configured so that the first locking surface 283, the second locking surface 285 and the fifth locking surface 385 are abuttingly engaged with the inner wall surface of the third wide locking groove 290.

By such engagement of the first locking surface 283 of the fifth lead frame 351 with the inner wall surface of the third wide locking groove 290, it becomes possible to inhibit the third frame main body section 262 of the fifth lead frame 351 from moving axially toward the rear end side. Further, by engagement of the second locking surface 285 and the fifth locking surface 385 of the fifth lead frame 351 with the inner wall surface of the third wide locking groove 290, it becomes possible to inhibit the third frame main body section 262 of the fifth lead frame 351 from moving in the direction apart from the inner surface of the third insertion hole 284.

Further, the sixth lead frame 353 has the first locking surface 433 and the second locking surface 435, and the first locking surface 433 and the second locking surface 435 are abuttingly engaged with the inner wall surface of the third narrow locking groove 291.

By such engagement of the first locking surface 433 of the sixth lead frame 353 with the inner wall surface of the third narrow locking groove 291, it becomes possible to inhibit the sixth frame main body section 412 from moving axially toward the rear end side. Further, by engagement of the second locking surface 435 of the sixth lead frame 353 with the inner wall surface of the third narrow locking groove 291, it becomes possible to inhibit the sixth frame main body section 412 from moving in the direction apart from the inner surface of the third insertion hole 284.

Namely, movement of the third frame main body section 262 of the fifth lead frame 351 and movement of the sixth frame main body section 412 of the sixth lead frame 353 can be inhibited even in case an external force is applied to the fifth lead frame 351 and the sixth lead frame 353, thus making it possible to prevent the relative positions of the fifth lead frame 351 and the detection element 4 and the relative positions of the sixth lead frame 353 and the detection element 4 from being varied.

Accordingly, by the third embodiment, a variation in the relative positions of the lead frame and the detection element 4 can be prevented even in case an inadequate external force is applied to the lead frames at the time of use of the fifth lead frame 351 and the sixth lead frame 353 which are formed smaller in the width side and in the thickness, and the electrical connection of the lead frames with the electrode terminal sections 30, 31, 32, 34, 36 can be maintained suitably.

As a result, at the time of the assembly work of assembling the detection element 4, the lead frames and the third separator 282 together, buckling of the lead frames is hard to be caused, therefore the frequency at which a defective is caused in the sensor production work can be decreased, and the sensor production efficiency can be improved.

Then, a fourth wide-range air/fuel ratio sensor (hereinafter also referred to as a fourth air/fuel ratio sensor) with a sixth lead frame 353 and a seventh lead frame 511 according to the fourth embodiment will be described.

In the meantime, since the fourth air/fuel ratio sensor is different from the air/fuel ratio sensor 2 of the first embodiment in that a lead frame and separator are formed into different shapes but other members (metallic housing member, detection element, etc.) are similar in shape, description will hereinafter be made mainly to the lead frame and the separator.

The fourth air/fuel ratio sensor includes a sixth lead frame 351, a seventh lead frame 511 and a fourth separator 382. The sixth lead frame 353 of those constituent parts is similar to that described in the third embodiment, so description thereto is omitted herein.

First, the fourth separator 382 will be described.

Figure 12:
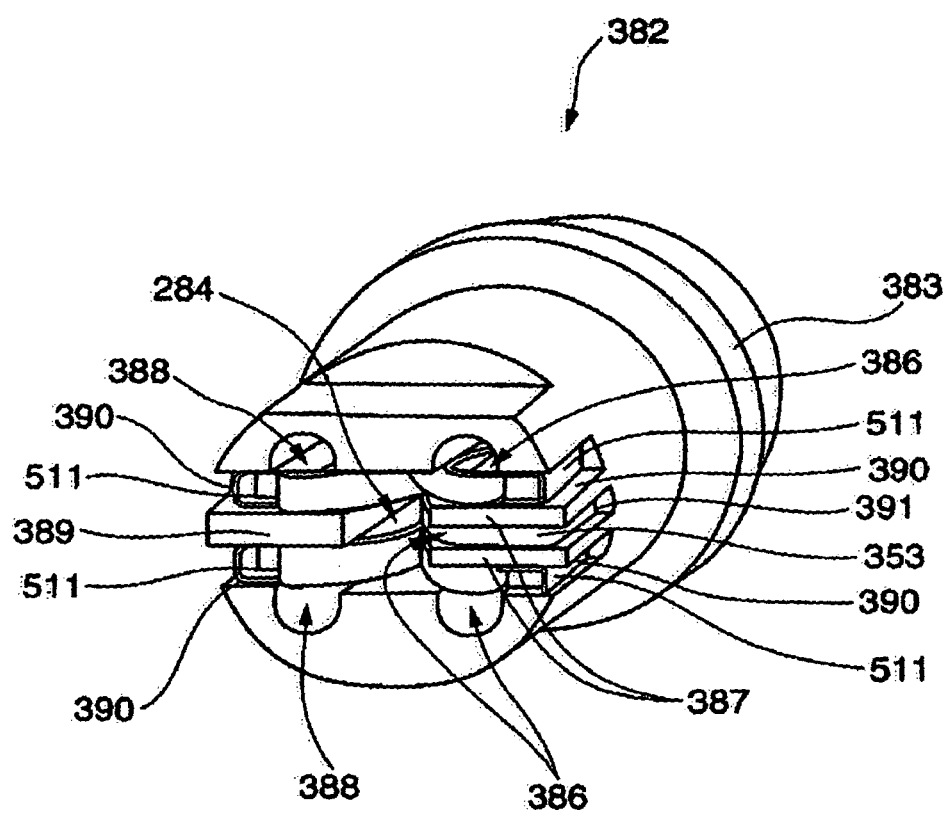
FIG. 12 is a perspective view showing an external appearance of a fourth separator.

In FIG. 12 is shown a perspective view of an external appearance of the fourth separator 382 when observed from the front end side thereof. In the meantime, in FIG. 12, the fourth separator 382 in the state where the sixth lead frame 353 and the seventh lead frame 511 are disposed in a fourth insertion hole 384 is shown in a perspective view.

As shown in FIG. 12, the second separator 382 is formed into a tubular shape having the fourth insertion hole 384 extending axially therethrough and has a fourth flange portion 383 protruding axially outward from an external surface thereof. The fourth separator 382 is abuttingly engaged at the fourth flange portion 383 with the outer tube side support portion 64 of the outer tube 44 and thereby disposed inside the outer tube 44. In the meantime, the outer tube side support portion 64 is formed so as to protrude inward of the outer tube 44 (refer to FIG. 1).

At the inner wall surface of the fourth insertion hole 384, which faces the first plate surface 21 (not shown) of the detection element 4 are formed two first rib portions 387 that protrude inward. The first rib portions 387 are provided to serve as lead frame boundary portions inside the insertion hole for forming boundaries of three frame disposition grooves 386 for disposing two seven lead frames 511 and one sixth lead frame 353 separately and in a state of being electrically insulated from each other. The three frame disposition grooves 386 are formed at the positions corresponding to the electrode terminal sections 30, 31 and 32 at the first plate surface 21 of the detection element 4.

Further, at the inner wall surface of the fourth insertion hole 384, which faces the second plate surface 23 of the detection element 4 (not shown), is formed one second rib portion 389 that protrudes inward. The second rib portion 389 is provided to serve as a lead frame boundary portion inside the insertion hole for forming a boundary of two wide frame disposition holes 388 for disposing two seventh lead frames 511 separately and in a state of being electrically insulated from each other. The two wide frame disposition grooves 388 are formed at the positions corresponding to the electrode terminal sections 34, 36 at the second plate surface 23 of the detection element 4.

The first rib portion 387 and the second rib portion 389 have a function of preventing the lead frames disposed in the adjacent frame disposition grooves from contacting each other and can prevent the adjacent lead frames from being electrically connected to each other and thereby prevent the electrical path from being deteriorated.

Further, the fourth separator 382 has at the front end surface (this side surface in the figure) fourth wide locking grooves 390 and fourth narrow locking grooves 391 that are joined to the front end side opening portion of the third insertion hole 284.

The fourth wide locking groove 390 has a radial groove section that is formed so as to extend from the front end side opening portion of the fourth insertion hole 384 axially outward of the fourth separator 382 and an axial groove section that is formed so as to communicate the radial groove section and extend toward the rear end side of the fourth separator 382. Further, the fourth wide locking groove 390 is formed so as to be capable of disposing therein a seventh frame locking section 519 of the seventh lead frame 511, which will be described later.

The fourth narrow locking groove 391 has a radial groove portion that is formed to extend from the front end side opening portion of the fourth insertion hole 384 radially outward of the fourth separator 382. Further, the fourth narrow locking groove 391 is formed so as to be capable of disposing therein the first narrow frame connection portion 421 and the second narrow frame connection portion 423 of the sixth lead frame 353, which will be described later.

In the meantime, the fourth narrow locking groove 391 is formed at a portion connected to central one of the three narrow frame disposition grooves 386 that are arranged side by side.

Then, the seventh lead frame 511 will be described.

Figure 13:
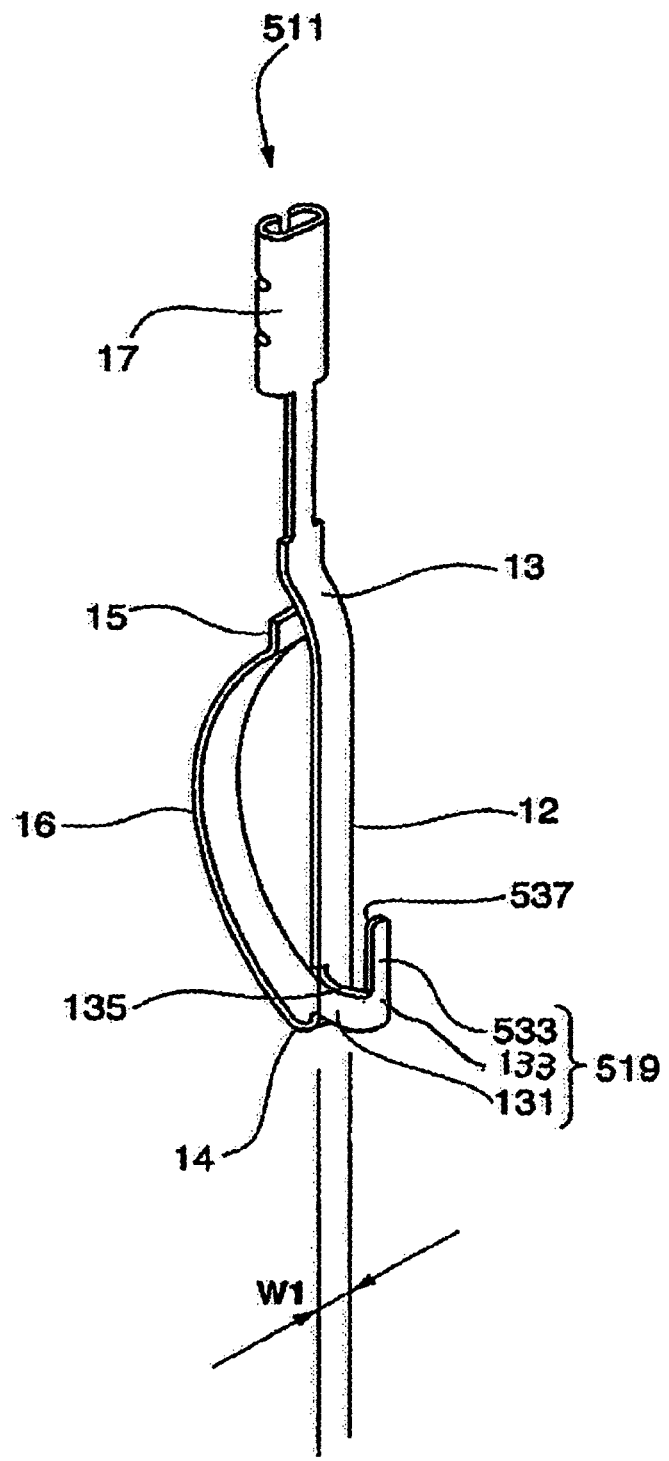
FIG. 13 is a perspective view showing an external appearance of a seventh lead frame.

FIG. 13 is a perspective view showing an external appearance of the seventh lead frame 511. The seventh lead frame 511 is configured so as to be substantially the same as the first lead frame 11 except for a seventh frame locking section 519 that is provided in place of the first frame locking section 19 of the first lead frame 11. In the meantime, the portions common to the seventh lead frame 511 and the first lead frame 11 are designated by the same references characters as those of the first lead frame 11.

The seventh frame locking section 519 is configured so as to include a first extension portion 131 shaped similarly to the first frame locking section 19 and a seventh extension portion 533 having such a shape that is obtained by enlarging the second extension portion 133 of the first frame locking section 19 axially toward the rear end side.

Of those portions, the first extension portion 131 is configured so as to extend in the direction of an intervening space between the frame main body section 12 and the element abutment section 16 and in the direction apart from the element abutment section 16.

Of the seventh frame locking section 519, the first extension portion 131 and the seventh extension portion 533 have a first locking surface that faces axially toward the rear end side of the frame main body section 12 and the seventh extension portion 533 has a seventh locking surface 537 that faces in the direction of an intervening space between the frame main body section 12 and the element abutment section 16 and toward the element abutment section 16 side.

As shown in FIG. 12, in case the seventh lead frame 511 is disposed in the fourth insertion hole 384 of the seventh lead frame 511, the seventh frame locking section 519 of the seventh lead frame 511 is disposed in the fourth wide locking groove 390 of the fourth separator 382. As a result, the first locking surface 135 and the seventh locking surface 537 of the seventh frame locking section 519 is put into a condition of being engaged with the inner wall surface of the fourth wide locking groove 390.

Further, in case the sixth lead frame 353 is disposed in the fourth insertion hole 384, the first narrow frame connection portion 421 and the second narrow frame connection portion 423 of the sixth lead frame 353 are disposed in the fourth narrow locking groove 391 of the fourth separator 382. As a result, the first locking surface 433 of the first narrow frame connection portion 421 and the second locking surface 435 of the second narrow frame connection portion 423 are put into a condition of being engaged with the inner wall surface of the fourth locking groove 391.

In the meantime, the seventh lead frame 511 is disposed in the fourth insertion hole 384 through insertion into the fourth insertion hole 384 of the fourth separator 384 together with the lead wire 46 after the lead wire connection section 17 is connected with the lead wire 46. Further, the sixth lead frame 353 is disposed in the fourth insertion hole 384 through insertion into the fourth insertion hole 384 of the fourth separator 382 together with the lead wire 46 after the sixth lead wire connection section 417 is connected with the lead wire 46.

By inserting the detection element 4 into the fourth insertion hole 384 of the fourth separator 382 in a state of having disposed therein the seventh lead frames 511 and the sixth lead frame 353 in the above-described manner, the element abutment sections 16 of the seventh lead frames 511 can be electrically connected with the electrode terminal sections 30, 32, 34, 36 of the detection element 4, and the sixth element abutment section 416 of the sixth lead frame 353 can be electrically connected with the electrode terminal section 31 of the detection element 4.

In the meantime, in the fourth embodiment, the seventh lead frame 511 and the sixth lead frame 353 correspond to the metallic terminal members described in "what is claimed is" and the fourth insertion hole 384 correspond to the element insertion hole. Further, of the seventh lead frame 511, the seventh extension portion 533 of the seventh frame locking section 519 corresponds to the second extension portion described in "what is claimed is" and the seventh locking surface 537 of the seventh extension portion 533 corresponds to the second locking surface described in "what is claimed is".

As having been described above, the fourth air/fuel ratio sensor of the fourth embodiment includes the seventh lead frame 511 with the first locking surface 135 and the seventh locking surface 537 and is configured so that the first locking surface 135 and the seventh locking surface 537 are engaged with the inner wall surface of the fourth wide locking groove 390.

By such engagement of the first locking surface 135 of the seventh lead frame 511 with the inner wall surface of the fourth wide locking groove 390, it becomes possible to inhibit the frame main body section 12 of the seventh lead frame 511 from moving axially toward the rear end side. Further, by engagement of the seventh locking surface 537 of the seventh lead frame 511 with the inner wall surface of the fourth wide locking groove 390, it becomes possible to inhibit the frame main body section 12 of the seventh lead frame 511 from moving in the direction apart from the inner surface of the fourth insertion hole 384.

Further, the sixth lead frame 353 has the first locking surface 433 and the second locking surface 435, and the first locking surface 433 and the second locking surface 435 are abuttingly engaged with the inner wall surface of the fourth narrow locking groove 391.

By such engagement of the first locking surface 433 of the sixth lead frame 353 with the inner wall surface of the fourth narrow locking groove 391, it becomes possible to inhibit the sixth frame main body section 412 from moving axially toward the rear end side. Further, by engagement of the second locking surface 435 of the sixth lead frame 353 with the inner wall surface of the fourth narrow locking groove 391, it becomes possible to inhibit the sixth frame main body section 412 from moving in the direction apart from the inner surface of the fourth insertion hole 384.

Namely, movement of the frame main body section 12 of the seventh leaf frame 511 and movement of the sixth lead frame main body section 412 of the sixth lead frame 353 can be inhibited even in case an external force is applied to the seventh lead frame 511 and the sixth lead frame 353, thus making it possible to prevent the relative positions of the seventh lead frame 511 and the detection element 4 and the relative positions of the sixth lead frame 353 and the detection element 4 from being varied.

Accordingly, by the fourth embodiment, a variation in the relative positions of the lead frame and the detection element 4 can be prevented even in case an inadequate external force is applied to the lead frames at the time of use of the seventh lead frame 511 and the sixth lead frame 353 which are formed smaller in the width side and in the thickness, and the electrical connection of the lead frames with the electrode terminal sections 30, 31, 32, 34, 36 can be maintained suitably.

As a result, at the time of the assembly work of assembling the detection element 4, the lead frames and the fourth separator 382 together, buckling of the lead frames is hard to be caused, therefore the frequency at which a defective is caused in the sensor production work can be decreased, and the sensor production efficiency can be improved.

While the embodiments of the present invention have been described as above, the invention is not limited thereto but can otherwise be embodied variously.

For example, regarding the metallic terminal member having the wide protrusion portions at the both sides of the second connection portion, the wide protrusion portions need not be of the same protrusion size but can be different in the protrusion size from one another. This makes it possible to prevent the rib portion of the separator from becoming partially too thin and obtain a sensor whose separator is hard to be damaged. Further, by the provision of two wide protrusion portions, the second locking surface can have a large area and movement of the frame main body section can be inhibited even when an inadequate external force is applied to the metallic terminal member, thus making it possible to prevent the relative positions of the metallic terminal member and the detection element from being varied. Further, since the provision of two wide protrusion portions makes it possible to prevent the metallic terminal member from going apart from the inner surface of the element insertion hole of the separator more assuredly, buckling of the metallic terminal member at the time of insertion of the detection element into the element insertion hole of the separator can be prevented.

Further, in order to maintain the rotational position of the separator relative to the outer tube constant, the separator may be formed with an engagement portion for positioning. By engaging the engagement portion for positioning with a predetermined engagement portion of the outer tube, the rotational position of the separator relative to the outer tube can be maintained constant. As an example of the engagement portion for positioning can be enumerated a cut portion 181 shown in FIG. 8.

Further, for engagement of the frame locking section of the metallic terminal member with the separator, the separator may be formed with a partition wall located between the frame locking section and the element insertion hole without being formed with the locking groove so that the frame locking section is engaged with the partition wall. In the meantime, it is not necessary to form the partition wall in place of the locking groove but together therewith.

Further, the sensor to which the present invention is applied is not limited to a sensor formed with the electrode terminal sections by five but the present invention can be applied to a sensor having an detection element with four electrode terminal sections or less or six electrode terminal sections or more.

The invention claimed is:

1. A sensor comprising:
    a detection element in the form of an axially extending plate, having a front end side to face an object to be measured and formed with an electrode terminal section at a rear end side;
    a separator made of an insulating material and having an element insertion hole accommodating the rear end side of the detection element; and
    a metallic terminal member interposed between the detection element and an inner surface of the element insertion hole of the separator;
    characterized in that:
    the metallic terminal member is formed from a metallic sheet material and having an axially extending frame main body section, an element abutment section extending while being bent to change the direction of extension, from a front end of the frame main body section axially toward a rear end side of the frame main body section and contacting the electrode terminal section of the detection element thereby being electrically connected thereto to form a current path, and a frame locking section having a first locking surface facing axially toward a rear end side of the frame main body section and a second locking surface facing in the direction of an intervening space between the frame main body section and the element abutment section and toward the element abutment section; and
    the separator has a locking groove for disposition of the frame locking section and engages at an inner wall surface of the locking groove with the first locking surface and the second locking surface.

2. A sensor according to claim 1, wherein the locking groove is formed at a front end surface of the separator.

3. A sensor according to claim 1, wherein the metallic terminal member is configured so that a frame abutment portion of the element abutment section, which is positioned closer to a rear end of the frame main body section than an end portion of the element abutment section, which is connected to the front end of the frame main body section, is not abuttingly engaged with the frame main body section when the metallic terminal member is in a free state before being electrically connected to the electrode terminal section of the detection element, while the frame abutment portion is abuttingly engaged with the frame main body section when the element abutment section is electrically connected to the electrode terminal section and resiliently deformed toward the frame main body section.

4. A sensor according to claim 1, wherein the frame locking section includes a first connection portion extending from a front end side portion of the frame main body section in the direction apart from the element abutment section, a second connection portion extending from an end of the first connection portion on the side remoter from the element abutment section, axially toward the front end, and a wide protrusion portion protruding from the second connection portion in the width direction of the second connection portion, and wherein the first connection portion is formed with the first locking surface, and the wide protrusion portion is formed with the second locking surfaces.

5. A sensor according to claim 4, wherein the wide protrusion portion is formed so as to be asymmetrical about a center axis of the second connection portion.

6. A sensor according to claim 1, wherein the frame locking section includes a first extension portion extending from a front end side portion of the frame main body section in the direction apart from the element abutment section and a second extension portion extending from an end of the first extension portion on the side remoter from the element abutment section in parallel with the frame main body section, and wherein at least one of the first extension portion and the second extension portion is formed with the first locking surface and the second extension portion is formed with the second locking surface.

7. A sensor according to claim 6, wherein at least two of the frame locking sections are provided so as to extend from different places of a front end side portion of the frame main body section.

8. A sensor according to claim 1, wherein the frame locking section includes a first frame connection portion extending from a front end side portion of the frame main body section in the direction apart from the element abutment section, a second frame connection portion extending from an end of the first connection portion on the side remoter from the element abutment section, axially toward a rear end side of the frame main body section, and a third frame connection portion extending from an end of the second connection portion on the side opposite to the side for connection with the first frame connection portion so as to be connected to the element abutment section, and wherein the first frame connection portion is formed with the first locking surface and the second frame connection portion is formed with the second locking surface.

9. A method of producing a sensor including a detection element in the form of an axially extending plate, having a front end side to face an object to be measured and formed with an electrode terminal section at a rear end side, a separator made of an insulating material and having an element insertion hole accommodating the rear end side of the detection element, and a metallic terminal member interposed between the detection element and an inner surface of the element insertion hole of the separator, wherein the metallic terminal member is formed from a metallic sheet material and having an axially extending frame main body section, an element abutment section extending while being bent to change the direction of extension, from a front end of the from the frame main body section axially toward a rear end side of the frame main body section and contacting the electrode terminal section of the detection element thereby being electrically connected thereto to form a current path, and a frame locking section having a first locking surface facing axially toward a rear end side of the frame main body and a second locking surface facing in the direction of an intervening space between the frame main body section and the element abutment section and toward the element abutment section, wherein the separator has a locking groove for disposition of the frame locking section, the method being characterized by comprising:

a first step of disposing at least the element abutment section of the metallic terminal member within the element insertion hole of the separator and disposing the frame locking section within the locking groove, thereby engaging the first locking surface and the second locking surface with the inner wall surface of the locking groove;

a second step of disposing the rear end side of the detection element, at which the detection element is formed with the electrode terminal section, at a front end side of the separator; and a third step of inserting the rear end side of the detection element into the element insertion hole of the separator and bringing the electrode terminal section of the detection element and the metallic terminal member into contact with each other.

10. A method of producing a sensor according to claim 9, wherein the metallic terminal member is configured so that a frame abutment portion of the element abutment section, which is positioned closer to a rear end of the frame main body section than an end portion of the element abutment section for connection with the front end of the frame main body section, is not abuttingly engaged with the frame main body section when the metallic terminal member is in a free state before being electrically connected to the electrode terminal section of the detection element, while the frame abutment portion is abuttingly engaged with the frame main body section when the element abutment section is electrically connected to the electrode terminal section and resiliently deformed toward the frame main body section, and wherein the first step includes disposing the metallic terminal member in a state of not receiving any external force within the element insertion hole of the separator and the third step includes inserting the detection element into the element insertion hole while pushing the detection element against the element abutment section, thereby resiliently deforming the element abutment section toward the frame main body section and abuttingly engaging the frame abutment portion of the element abutment section with the frame main body section.

* * * * *